(12) United States Patent
Sajic et al.

(10) Patent No.: US 6,218,346 B1
(45) Date of Patent: Apr. 17, 2001

(54) METHODS FOR CLEANING, CONDITIONING AND STYLING HAIR

(75) Inventors: Branko Sajic, Lincolnwood; Y. Kameshwer Rao, Skokie, both of IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 08/943,673

(22) Filed: Oct. 3, 1997

Related U.S. Application Data

(63) Continuation-in-part of application No. PCT/US96/14358, filed on Sep. 5, 1996, now abandoned, which is a continuation-in-part of application No. 08/632,013, filed on Apr. 15, 1996, now Pat. No. 6,017,860.

(51) Int. Cl.$^7$ .................................................. A61K 7/075
(52) U.S. Cl. ........................ 510/124; 510/121; 510/123; 510/476; 8/137; 132/203; 424/70.11; 424/70.13; 424/70.19; 424/70.21; 424/70.28; 424/70.31
(58) Field of Search .................... 510/119, 123, 510/121, 124, 476; 8/137; 424/70.11, 70.13, 70.15, 70.16, 70.19, 70.27, 70.31, 70.21, 70.28; 132/203

(56) References Cited

U.S. PATENT DOCUMENTS

| | | | |
|---|---|---|---|
| 4,210,161 | 7/1980 | Wagman | 132/7 |
| 4,247,538 | 1/1981 | Barker | 424/70.21 |
| 4,719,099 | * 1/1988 | Grollier et al. | 424/47 |
| 4,940,576 | * 7/1990 | Walsh | 424/70.11 |
| 5,034,218 | * 7/1991 | Duvel | 424/70.12 |
| 5,298,240 | 3/1994 | Schroder et al. | 424/70.19 |
| 5,575,991 | 11/1996 | Kischka et al. | 424/70.2 |
| 5,656,200 | * 8/1997 | Boettcher et al. | 424/70.11 |
| 5,679,330 | * 10/1997 | Matsuo et al. | 424/70.19 |

FOREIGN PATENT DOCUMENTS

| | | |
|---|---|---|
| 0 260 641 A2 | 3/1988 | (EP) . |
| 0 335 404 A2 | 10/1989 | (EP) . |
| 0 370 764 A2 | 5/1990 | (EP) . |
| 0 490 053 A1 | 6/1992 | (EP) . |
| 0 636 357 A1 | 2/1995 | (EP) . |
| 0 638 637 A2 | 2/1995 | (EP) . |
| 0 642 782 A2 | 3/1995 | (EP) . |
| 0 651 048 A2 | 5/1995 | (EP) . |
| 0 698 660 A2 | 2/1996 | (EP) . |
| 3188195 | 8/1991 | (JP) . |
| WO 94/16668 | 8/1994 | (WO) . |
| WO 96/05807 | 2/1996 | (WO) . |
| WO 97/38673 | 10/1997 | (WO) . |

* cited by examiner

Primary Examiner—Caroline D. Liott
(74) Attorney, Agent, or Firm—McDonnell Boehnen Hulbert & Berghoff

(57) ABSTRACT

Disclosed are hair care compositions and methods for preparing such compositions which provide the benefits of cleaning, conditioning, curl retention, styling and setting properties simultaneously to hair in the application of a single product. The hair care compositions contain fatty alkyl amine salts, long chain quaternary ammonium salts and mixtures thereof of anionic styling polymers in a non-anionic surfactant system, wherein the surfactant system contains nonionic surfactants, semi-polar nonionic surfactants, amphoteric surfactants and mixtures thereof. The styling, setting and conditioning agents are present in the form of fatty alkyl amine salts or fatty quaternary ammonium salts which form anionic styling polymer particulate networks upon dilution in water. These networks are dispersed in the aqueous non-anionic surfactant system and are stabilized and thickened by optional swellable polymer thickening agents. Hair care compositions of the present invention can be made in the form of structured liquids, pearlescent/opaque isotropic liquid and/or translucent/clear isotropic liquids. The hair care compositions of the present invention, which allow for re-styling of the hair by wetting the hair with water, contain no anionic surfactants, silicones, solvents or cationic polymeric conditioning agents. Furthermore, multiple application of these hair care compositions does not produce a noticeable build-up on the hair.

13 Claims, 1 Drawing Sheet

METHODS FOR CLEANING, CONDITIONING AND STYLING HAIR

This application is a continuation-in-part of International Application PCT/US96/14358, with an international filing date of Sep. 5, 1996, now abandoned, which is a continuation-in-part of U.S. application Ser. No. 08/632,013 filed Apr. 15, 1996, now U.S. Pat. No. 6,017,860.

BACKGROUND OF THE INVENTION

1. Field of the Invention

The present invention relates to hair care compositions and methods for preparing such compositions which provide the multiple benefits of cleaning, conditioning, styling, curl retention, bodifying, stiffness and setting properties to the hair in the application of a single product to the hair. More specifically, the invention relates to hair-care compositions containing a styling polymer and a cationic compound in a non-anionic surfactant system. The surfactant system contains nonionic surfactants, semi-polar nonionic surfactants, amphoteric surfactants and mixtures thereof. The hair care compositions of the present invention, when diluted in water during use, form and/or release the styling/conditioning agents to the hair in the form of macrofibrils or dispersed small complex particles.

2. Description of the Related Art

The process of hair care is multifaceted and generally involves washing, conditioning, and styling the hair, often as a three step process. The first step of the process involves the thorough cleaning of the hair with an initial application of shampoo. After the hair is cleaned and rinsed, the second step of the process involves conditioning the hair with a conditioner, which is applied to the hair and allowed to thoroughly penetrate into the hair. After a sufficient period of time, the residual conditioner is rinsed off the hair with water. Typically, conditioners contain cationic conditioning agents or suspended silicone conditioning agents which adhere to the hair follicle after the residual conditioning product is rinsed off the hair. The third step of the process optionally involves the application of styling agents to assist in arranging and forming the hair into a desired configuration.

The desirable results of the hair care process include a persistent look and feel of clean hair between washings, ease of combing, absence of static electricity, manageability, soft feel and shine. In general, these results are obtained by utilizing a hair conditioning product which is separate from the hair cleaning product. The use of two separate products for cleaning and conditioning of hair involves the use of a shampoo cleaning product and a separate rinse out conditioner or the use of a shampoo cleaning product and a separate leave-on conditioner. The use of two separate products in the hair care process is regarded as somewhat of an inconvenience to consumers.

A limited number of hair care products are available which clean as well as condition the hair by the use of one product, i.e., a two-in-one conditioning shampoo. Certain two-in-one conditioning shampoos typically contain water, anionic surfactants, foam stabilizers, insoluble nonvolatile silicone conditioning agents and silicone suspending agents. Other such products contain cationic conditioning agents in place of silicone. However, all of these two-in-one products have various limitations. These limitations are well known in the art.

Hair care products which impart hair styling, i.e., shape and style retention, are numerous. Such products typically fall into two catagories: (1) products that chemically alter hair, and (2) products that temporarily alter the shape or style of hair style. Each of these methods has its own problems. For example, temporary styling requires a separate application step following cleaning and/or conditioning of the hair. Additionally, many of the polymer based styling aids tend to make the hair feel undesirably sticky and stiff after application.

Still other hair care products are available which simultaneously clean, condition and control dandruff, i.e, a 3-in-1 anti-dandruff shampoo.

Since known two- and three-in-one hair care products have various limitations, a need exists for surfactant based hair styling shampoo compositions which are capable of delivering cleaning, foaming, conditioning, curl retention, body and styling properties to the hair in one application step, with limited or no build up of the compositions on the hair after multiple application, and at the same time are free of nonaqueous solvents. Avoiding the use of nonaqueous solvents in hair care compositions is highly desirable, from economical, environmental and consumer demand points-of-view. It is desired that new hair care compositions provide comparable or superior cleaning, foaming, conditioning, curl retention and styling properties to the hair in one application step, as compared to prior art hair care compositions and/or the use of two or more products in two or more application steps. Further, a need exists for compositions with the above described properties which are efficacious on fine, long, or chemically damaged hair.

SUMMARY OF THE INVENTION

The present invention provides hair care compositions that are substantially free of nonaqueous solvents, which impart cleaning, foaming, conditioning, curl retention and styling properties to the hair, comprising:

(a) from about 1 percent to about 80 percent by weight, based on the total weight of the hair care composition, of a first surfactant member selected from the group consisting of nonionic surfactants, semi-polar nonionic surfactants, amphoteric surfactants and mixtures thereof;

(b) from about 0.1 percent to about 10 percent by weight, based on the total weight of the hair care composition, of a cationic surfactant; and (c) from about 0.001 percent to about 10 percent by weight, based on the total weight of the hair care composition, of an anionic polymer member selected from the group consisting of polymers with one or more carboxylic acid groups, polymers with one or more carboxylic acid alkali metal salt groups, polymers with one or more sulfate groups, polymers with one or more sulfonate groups and mixtures thereof.

The cationic surfactant employed in the invention is represented by Formula 1:

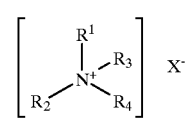

wherein $R_1$, $R_2$, $R_3$, and $R_4$ independently represent hydrocarbyl chains of from about 1 to about 30 carbon atoms, or hydrocarbyl chain having from about 1 to about 30 carbon atoms optionally containing one or more aromatic, ether, ester, amido, or amino moieties present as substituients or as linkages in the hydrocarbyl chain, where at least one of the $R_1$–$R_4$ groups is optionally substituted with at least one or more hydrophilic moieties independently selected from alkoxy, polyoxyalkylene, alkylamido, hydroxyalkyl, and alkylester; and X is a soluble salt forming anion.

The hair care compositions of the present invention optionally contain from about 0.1 percent to about 10 percent by weight, based on the total weight of the hair care composition, of a swellable polymer thickening agent.

The present invention also provides methods for treating hair comprising applying to hair a composition according to the invention.

The present invention further provides methods for preparing hair care compositions comprising combining, in any order, (a) from about 1 percent to about 80 percent by weight, based on the total weight of the hair care composition, of a first surfactant member selected from the group consisting of nonionic surfactants, semi-polar nonionic surfactants, amphoteric surfactants and mixtures thereof;

(b) from about 0.1 percent to about 10 percent by weight, based on the total weight of the hair care composition, of a cationic surfactant; and (c) from about 0.001 percent to about 10 percent by weight, based on the total weight of the hair care composition, of an anionic polymer member selected from the group consisting of polymers with one or more carboxylic acid groups, polymers with one or more carboxylic acid alkali metal salt groups, polymers with one or more sulfate groups, polymers with one or more sulfonate groups and mixtures thereof.

In addition, the invention encompasses methods for preparing a styling and conditioning agent comprising combining a cationic surfactant with an anionic polymer.

The invention also encompasses a styling and conditioning agent prepared by the reaction of an anionic polymer with a cationic surfactant.

The present invention provides methods for preparing a hair care composition comprising combining (a) from about 1 percent to about 80 percent by weight, based on the total weight of the hair care composition, of the first surfactant member described above; and (b) from about 0.001 percent to about 20 percent by weight, based on the total weight of the hair care composition, of the styling and conditioning agent of the invention.

The invention further provides a complex produced by the combination of an anionic polymer and a cationic surfactant; wherein the complex has a molecular weight of at least 100,000, and where the anionic polymer is selected from the group consisting of polymers with one or more carboxylic acid groups, polymers with one or more carboxylic acid alkali metal salt groups, polymers with one or more sulfate groups, polymers with one or more sulfonate groups and mixtures thereof.

As noted, the anionic polymer and the cationic surfactant are capable of combining to form a complex, and the anionic polymer has a molecular weight sufficient to form a complex with a molecular weight of at least about 100,000. Since the cationic surfactant generally cannot have a molecular weight of greater than about 50,000, the molecular weight of the anionic polymer is at least about 50,000.

The present invention relates to a compound of Formula 2:

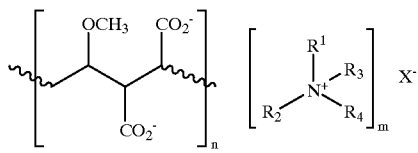

wherein n is an integer from about 1–500,000; m is an integer from about 1–1,000,000; $R_1$, $R_2$, $R_3$, and $R_4$ independently represent hydrocarbyl chains of from about 1 to about 30 carbon atoms, or hydrocarbyl chain having from about 1 to about 30 carbon atoms and optionally containing one or more aromatic, ether, ester, amido, or amino moieties present as substituients or as linkages in the hydrocarbyl chain, where at least one of the $R_1$–$R_4$ groups is optionally substituted with at least one or more hydrophilic moieties independently selected from alkoxy (preferably $C_1$–$C_3$ alkoxy), polyoxyalkylene (preferably $C_1$–$C_3$ polyoxyalkylene), alkylamido, hydroxyalkyl, and alkylester.

The present invention relates to a compound of Formula 3:

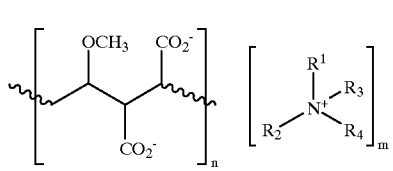

wherein n is an integer from about 1–500,000; m is an integer from about 1–500,000; wherein R is alkyl, alkenyl, alkynyl, aryl, alkylaryl, and mixtures thereof; $R_1$, $R_2$, $R_3$, and $R_4$ independently represent hydrocarbyl chains of from about 1 to about 30 carbon atoms, or hydrocarbyl chain having from about 1 to about 30 carbon atoms and optionally containing one or more aromatic, ether, ester, amido, or amino moieties present as substituients or as linkages in the hydrocarbyl chain, where at least one of the $R_1$–$R_4$ groups is optionally substituted with at least one or more hydrophilic moieties independently selected from alkoxy (preferably $C_1$–$C_3$ alkoxy), polyoxyalkylene (preferably $C_1$–$C_3$ polyoxyalkylene), alkylamido, hydroxyalkyl, and alkylester.

In a preferred embodiment, the invention provides hair care compositions comprising:

(a) from about 8 percent to about 20 percent by weight, based on the total weight of the hair care composition, of a first surfactant member selected from the group consisting of nonionic surfactants, semi-polar nonionic surfactants, amphoteric surfactants and mixtures thereof;

(b) from about 0.5 percent to about 5 percent by weight, based on the total weight of the hair care composition, of a cationic surfactant.

Another preferred embodiment of the invention encompasses hair care compositions comprising:

(a) from about 10 percent to about 16 percent by weight, based on the total weight of the hair care composition, of a first surfactant member selected from the group consisting of nonionic surfactants, semi-polar nonionic surfactants, amphoteric surfactants and mixtures thereof;

(b) from about 1.0 percent to about 3.0 percent by weight, based on the total weight of the hair care composition, of a cationic surfactant.

The hair care compositions of the present invention optionally contain from about 0.001 percent to about 10 percent of optional ingredients selected from the group comprising anti-dandruff agents, fragrance oils, perfumes, coloring agents, dyes, sequestering agents, preservatives, pearlescent/suspending agents, thickener, viscosity modifiers, pH adjusting agents, gelling agents, opacifying agents, foam stabilizing auxiliary surfactants, silicone oils, non-volatile/nonionic silicone conditioning agents, vitamins, protein, sunscreen agents and mixtures thereof.

DETAILED DESCRIPTION OF THE INVENTION

Figure 1:
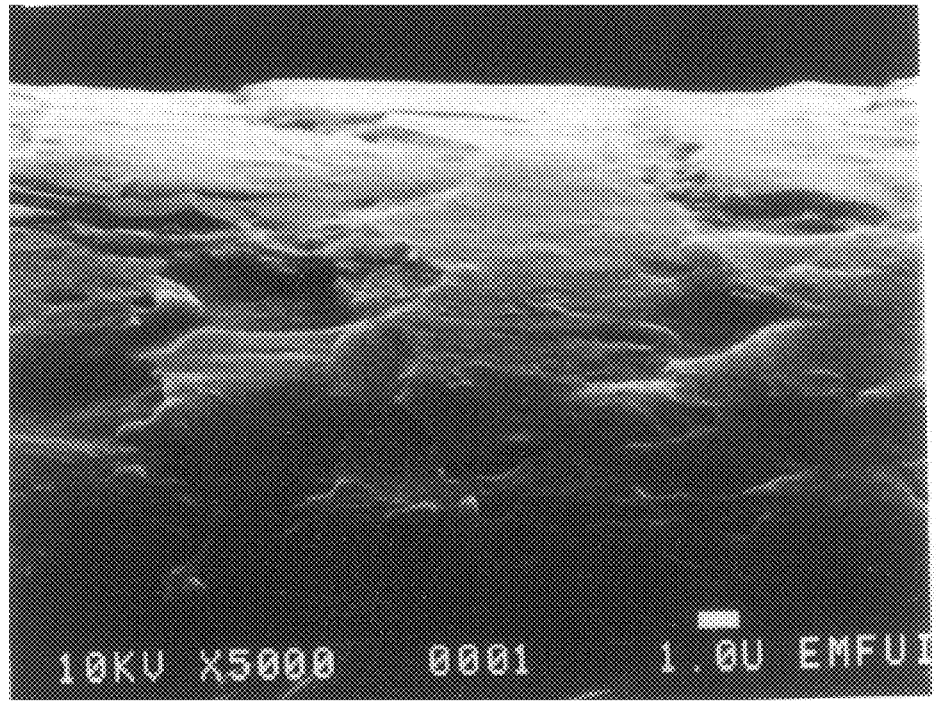
FIG. 1 is a scanning electron micrograph at 5000X magnification of normal hair treated two times with Formulation #46.
Figure 2:
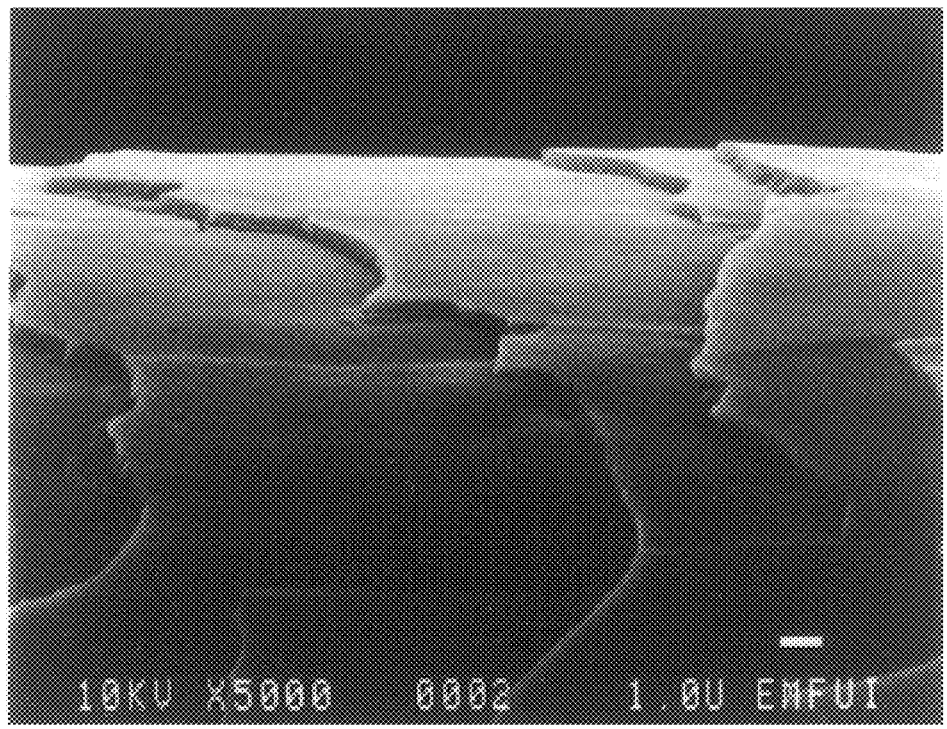
FIG. 2 is a scanning electron micrograph at 5000X magnification of normal hair treated with a leading 2-in-1 conditioning shampoo (Pert Plus Shampoo for Normal Hair).

By isotropic liquid is meant an optically transparent solution that does not transmit visible light when viewed under a polarized light microscope.

Anisotropic liquid as used herein refers to optically turbid solutions or dispersions that transmit visible light when viewed under a polarized light microscope. Such solutions are identified as multiple Malthesan crosses.

It has been surprisingly discovered that shampooing hair with the compositions described above provides superior cleaning, foam generation, conditioning, styling, setting and curl retention properties to the hair in a single product application. These compositions are substantially free of nonaqueous solvents (solvents other than water) and (with certain exceptions) anionic surfactants. Thus, the compositions of the present invention may contain minor amounts, i.e., up to about 5% by weight of the composition, of nonaqueous solvents, such as alcohols, glycols, etc. Such nonaqueous solvents are usually impurities present the surfactant components or other components of the hair care compositions. It is preferable to the maintain the level of nonaqueous solvents in the compositions below about 5 percent, based on the total amount of active components in the composition and preferably below 5 percent, based on the total weight of the composition. Most preferably, the amount of nonaqueous solvents is less than about 2 percent, based on the total weight of the composition.

In all systems of the invention, the cationic surfactant may be combined with the anionic styling polymer to form the complex.

Hair care compositions of the present invention have the desirable characteristic of allowing for restyling of the hair after application. During restyling, hair which has been previously treated with a hair care composition of the present invention is moistened with water, combed and allowed to air dry or is dried with a mechanical means, and the hair arranged and formed into a desired configuration.

Additionally, during restyling, hair which has been previously treated with a hair care composition of the present invention is moistened with water, optionally combed, set on rollers, allowed to air dry or is dried with a mechanical means, the rollers are removed and the hair is combed out to achieve the desired hair style.

The hair care compositions of the present invention are three-in-one compositions which comprise nonionic, amphoteric, and cationic surfactants, styling aides in the form of anionic polymers and alkali metal salts thereof, swellable polymer thickening agents and other optional ingredients. Significantly, these composition do not impart to the hair a sticky and/or heavily crusted feeling after application. Without being bound by any particular theory, it is believed that the benefits provided by the present compositions are achieved by dispersing the styling and conditioning system, wherein the styling and conditioning system comprises fatty alkyl amine salts, long chain quaternary ammonium salts, and mixtures thereof, of anionic styling polymers, in the non-anionic surfactant(s). Again without being bound by any particularly theory, it is believed that the anionic styling polymers are completely solubilized as a fine dispersion in the aqueous non-anionic surfactant system and are generally electrolytically stable. An important discovery of the present invention resides in the stabilization and solubilization of the anionic polymer and cationic surfactants by the use of non-ionic and amphoteric surfactants in combination with swellable polymer thickening agents in the hair care composition, rather than the use of nonaqueous solvents to solubilize the hair styling polymer(s), as taught in the prior art.

In the compositions of the invention, the first surfactant member is present from about 2 percent to about 25 percent by weight, based on the total weight of the hair care composition; more preferably from about 8 percent to about 20 percent by weight, based on the total weight of the hair care composition. The second surfactant member is present from about 0.5 percent to about 5.0 percent by weight, based on the total weight of the hair care composition, more preferably from about 1.0 percent to about 3.0 percent by weight, based on the total weight of the hair care composition. The anionic polymer is present from about 0.001 percent to about 5.0 percent by weight, based on the total weight of the hair care composition, more preferably from about 0.3 percent to about 2.0 percent by weight, based on the total weight of the hair care composition.

The optional swellable polymer thickening agent is present from about 0.2 percent to about 3.0 percent by weight, based on the total weight of the hair care composition, more preferably from about 0.2 percent to about 2.0 percent by weight. Suitable swellable polymer thickening agents include, for example, methyl cellulose, ethyl cellulose, xanthan gum, gum arabic, gum karaya, guar gum, locust bean gum, ghatti gum, hydrolyzed starches, low molecular weight ethylene oxide polymers, low molecular weight propylene oxide polymers and mixtures thereof.

The hair care compositions of the present invention can be made in the form of opaque structured liquids, pearlescent/opaque isotropic liquids and/or translucent/clear isotropic liquids. These hair care compositions contain no anionic surfactants, solvents or cationic polymeric conditioning agents. Without being bound to any theory, it is believed that dispersed or solubilized amine salts and/or quaternary ammonium salts and solubilized anionic styling polymer acids or salts are present as separate entities in a concentrated product. Upon dilution and at typical use concentration, the viscosity of the system decreases and the micellar structure breaks thus releasing mobile surfactant monomers which interact with the anionic styling polymer to form a microfiber-like styling/conditioning complex. The complex appears as microfibers. The complex is a fatty alkyl amine salt, a long chain quaternary ammonium salt, or mixtures thereof, of the anionic styling polymer. Again without being bound by any particular theory, it is believed that the microfibers are positively charged fibrils or fibers possessing adhesion characteristics allowing the microfibers to be attracted to the negatively charged surface of the hair. The result is the formation of a continuous film on the hair, providing both conditioning and styling properties to the hair.

If so desired, the compositions of the present invention may be removed from the hair by treating the hair with a standard shampoo composition. The compositions of the present invention do not cause a build up of the aforementioned film on the hair after multiple application to the hair.

In a preferred embodiment of the present invention, the first surfactant member is a nonionic surfactant or an amphoteric surfactant or a mixture thereof. In such compositions, the first surfactant member is present from about 5% to about 25% by weight, based on the total weight of the hair care composition. In a more preferred embodiment of the present invention, the first surfactant member is a nonionic surfactant or an amphoteric surfactant present from about 8% to about 20% by weight, based on the total weight of the hair care composition.

Nonionic Surfactants

Suitable nonionic surfactants in accordance with the present invention are generally disclosed at column, 13 line 14 through column 16, line 6 of U.S. Pat. No. 3,929,678, the disclosure of which is incorporated herein by reference in its entirety. Generally, the nonionic surfactant is selected from the group comprising polyoxyethyleneated alkylphenols, polyoxyethyleneated straight chain alcohols, polyoxyethyleneated branched chain alcohols, polyoxyethyleneated polyoxypropylene glycols, polyoxyethyleneated mercaptans, fatty acid esters, glyceryl fatty acid esters, polyglyceryl fatty acid esters, propylene glycol esters, sorbitol esters, polyoxyethyleneated sorbitol esters, polyoxyethylene glycol esters, polyoxyethyleneated fatty acid esters, primary alkanolamides, ethoxylated primary alkanolamides, secondary alkanolamides, ethoxylated secondary alkanolamides, tertiary acetylenic glycols, polyoxyethyleneated silicones, N-alkylpyrrolidones, alkylpolyglycosides, alkylpolylsaccharides, EO–PO blockpolymers, polyhydroxy fatty acid amides, amine oxides and mixtures thereof. Further, exemplary, non-limiting classes of useful nonionic surfactants are listed below:

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to 12 carbon atoms in either a straight or branched chain configuration with the alkylene oxide. In a preferred embodiment, the ethylene oxide is present in an amount equal to from about 1 to about 25 moles of ethylene oxide per mole of alkyl phenol. Commercially available nonionic surfactants of this type include Igepal® CO-630, marketed by the GAF Corporation; and Triton® X-45, X-114, X-100 and X-102, all marketed by the Rohm and Haas Company.

2. The condensation products of aliphatic alcohols with from about 1 to about 25 moles of ethylene oxide. The alkyl chain of the aliphatic alcohol can either be straight or branched, primary or secondary, and generally contain from about 8 to about 22 carbon atoms. Particularly preferred are the condensation products of alcohols having an alkyl group containing from about 6 to about 11 carbon atoms with from about 2 to about 10 moles of ethylene oxide per mole of alcohol. Examples of commercially available nonionic surfactants of this type include Tergitol® 15-S-9 (the condensation products of $C_{11}$–$C_{15}$ linear alcohol with 9 moles of ethylene oxide), Tergitol® 24-L-6 NMW (the condensation products of $C_{12}$–$C_{14}$ primary alcohol with 6 moles of ethylene oxide with a narrow molecular weight distribution), both marketed by Union Carbide Corporation; Neodol® 91-8 (the condensation product of $C_9$–$C_{11}$ linear alcohol with 8 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 91-6 (the condensation product of $C_9$–$C_{11}$ linear alcohol with 6 moles of ethylene oxide), marketed by Shell Chemical Company, and Kyro® EOB (the condensation product of $C_{13}$–$C_{15}$ linear alcohol with 9 moles of ethylene oxide), marketed by the Procter and Gamble Company.

3. The condensation products of ethylene oxide with a hydrophobic base formed by the condensation of propylene oxide with propylene glycol. The hydrophobic portion of these compounds preferably has a molecular weight of from about 1500 to about 1880 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic® surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic® compounds, marketed by BASF.

5. Semi-polar nonionic surfactants are a special category of nonionic surfactants which include water-soluble amine oxides containing on alkyl moiety of from about 10 to about 18 carbon atoms and 2 moieties selected from the group comprising alkyl groups and hydroxyalkyl groups containing from about 1 to about 3 carbon atoms; and water-soluble sulfoxides containing alkyl moieties of from about 10 to about 18 carbon atoms and a moiety selected from the group comprising alkyl groups and hydroxylalkyl groups of from about 1 to about 3 carbon atoms.

6. Alkylpolysaccharides disclosed in U.S. Pat. No. 4,565,647, Lenado, issued Jan. 21, 1986, incorporated herein by reference, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally, the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units.

7. An ethyl ester ethoxylate and/or alkoxylate such as those described in U.S. Pat. No. 5,220,046, incorporated herein by reference. These material may be prepared according to the procedure set forth in Japanese Kokai patent application No. HEI 5 [1993]-222396. For example, they may be prepared by a one-step condensation reaction between an alkyl ester and an alkylene oxide in the present of a catalytic amount of magnesium together with another ion selected from the group of $Al^{+3}$, $Ga^{+3}$, $In^{+3}$, $Co^{+3}$, $Sc^{+3}$, $La^{+3}$ and $Mn^{+3}$. Optionally, and less desirably, there can be a polyalkyleneoxide chain joining the hydrophobic moiety and the polysaccharide moiety. The preferred alkyleneoxide is ethylene oxide. Typical hydrophobic groups include aLkyl groups, either saturated or unsaturated, branched or unbranched, containing from about 8 to about 18, preferably from about 12 to about 14 carbon atoms; n is 2 or 3, preferably 2; t is from about 0 to about 10, preferably 0; and x is from about 1.3 to about 10, preferably from about 1.3 to 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glucosyl units can then be attached between their 1-position and the preceding glycosyl units 2-, 3-, 4- and/or 6-position, preferably predominately the 2-position.

8. Other nonionic surfactants include alkoxylated mono- and diglycerides of fatty acids. Preferred are ethoxylated and/or propoxylated glycerides of fatty acids having from 6–40 carbon atoms. Suitable alkoxylated mono- and diglycerides of such acids are commercially available from Witco Corporation. Examples of such nonionic surfactants include Varonic LI-63 (PEG-30 Glyceryl Cocoate, Witco), Varonic LI-67 (PEG-80 Glyceryl Cocoate, Witco), Varonic LI-67, 75% (PEG-80 Glyceryl Cocoate, Witco), Varonic LI-42 (PEG-20 Glyceryl Tallowate, Witco), Varonic LI-48 (PEG-80 Glyceryl Tallowate, Witco), and Varonic LI-420, 70% (PEG-200 Glyceryl Tallowate, Witco).

9. Additional nonionic surfactants are alkoxylated alkyl esters of fatty acids. Preferred alkoxylated alkyl esters are ethoxylated and/or propoxylated methyl esters of fatty acids having from 8–40 carbon atoms. Suitable alkoxylated methyl esters of such acids are commercially available from Lion Corporation. Examples of such nonionic surfactants include $RCO_2(CH_2CH_2O)_nCH_3$ where R is $C_{12}$, and n is about 10.9 (commercially available from Lion Corporation, Japan, as LC-110M), and $RCO_2(CH_2CH_2O)_nCH_3$ where R is $C_{12}$, and n is about 14.6 (commercially available from Lion Corportaion, Japan, as LC-150M-92).

Amphoteric Surfactants

Suitable amphoteric surfactants are selected from the group comprising alkyl glycinates, propionates, imidazolines, amphoalkylsulfonates sold as "Miranol"® by Rhone Poulenc, N-alkylaminopropionic acids, N-alkyliminodipropionic acids, imidazoline carboxylates, N-alkylbetaines, amido propyl betaines, sarcosinates, cocoamphocarboxyglycinates, amine oxides, sulfobetaines, sultaines and mixtures thereof. Additional suitable amphoteric surfactants include cocoamphoglycinate, cocoamphocarboxyglycinate, lauramphocarboxyglycinate, cocoamphopropionate, lauramphopropionate, stearamphoglycinate, cocoamphocarboxypropionate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocamphopropylsulfonate, stearamphopropylsolfonate, oleoamphopropylsulfonate and the like.

Amine Oxide Surfactants

Amine oxide surfactants which are generally suitable for use in the present invention are alkylamine and amidoamine oxides. Examples of betaines and sultaines which are suitable for use in the present invention are alkyl betaines and sultaines sold as "Mirataine"® by Rhone Poulenc, "Lonzaine"® by Lonza, Inc., Fairlawn, N.J. Examples of betaines and sultaines are cocobetaine, cocoamidoethyl betaine, cocoamidopropyl betaine, lauryl betaine, lauramidopropyl betaine, palmamidopropyl betaine, stearamidopropyl betaine, stearyl betaine, coco-sultaine, lauryl sultaine, tallowamidopropyl hydroxysultaine and the like.

Cationic Surfactants

In a preferred embodiment of the present invention, the cationic surfactant is present from about 0.5 percent to about 5.0 percent, based on the total weight of the hair care composition. In a more preferred embodiment of the present invention, the cationic surfactant is present from about 1.0 percent to about 3.0 percent, based on the total weight of the hair care composition.

Generally, the cationic surfactant is a surfactant selected from fatty amine salts, fatty diamine salts, polyamine salts, quaternary ammonium compounds, polyoxyethyleneated fatty amines, quaternized polyoxyethyleneated fatty amines, amine oxides and mixtures thereof.

A variety of cationic surfactants useful as detersive surfactants and as conditioning agents are well know in the art. These materials contain amino or quaternary ammonium hydrophilic moieties which are positively charged when dissolved in the compositions of the present invention. Whether the cationic surfactant functions as a detersive surfactant or as a conditioning agent, or both, will depend upon the particular compound as is well understood by those skilled in the art. In general, compounds with longer chain length moieties attached to the cationic nitrogen tend to exhibit greater conditioning benefits. Cationic surfactants among those useful herein are disclosed in the following documents, all incorporated by reference herein: M. C. Publishing Co., *McCutcheon's Detergents & Emulsifiers,* (North American Ed., 1993); Schwartz et al., *Surface Active Agents, Their Chemistry and Technology,* New York; Interscience Publisher, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Cationic surfactants in the form of quaternary ammonium salts include dialkyldiethyl ammonium chlorides and trialkyl methyl ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from about 16 to about 18 carbon atoms). These types of cationic surfactants are useful as hair conditioning agents. Examples of quaternary ammonium salts useful herein include ditallowdimethyl ammonium chloride, ditallowdimethyl ammonium methyl sulfate, dihexadecyl dimethyl ammonium chloride, di-(hydrogenated tallow) dimethyl ammonium chloride, dioctadecyl dimethyl ammonium chloride, dieicosyl dimethyl ammonium chloride, didocosyl dimethyl ammonium chloride, di-(hydrogenated tallow) dimethyl ammonium acetate, dihexadecyl dimethyl ammonium chloride, dihexadecyl dimethyol ammonium acetate, ditallow dipropyl ammonium phosphate, ditallow dimethyl ammonium nitrate, di-(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride and tricetyl methyl ammonium chloride are particularly preferred quaternary ammonium salts. Preferred of the conventional cationic conditioning agents are cetyl trimethyl ammonium chloride, lauryl trimethyl ammonium chloride, tricetyl methyl ammonium chloride, stearyldimethyl benzyl ammonium chloride, and di-(partially hydrogenated tallow) dimethyl ammonium chloride; these materials may also provide anti-static benefits to the present compositions.

Salts of primary, secondary and tertiary fatty amines are also suitable cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrogen chloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated herein by reference.

Cationic surfactants which are especially useful in compositions of the present invention are quaternary ammonium or amino compounds having at least one N-radical containing one or more nonionic hydrophilic moieties selected from the group comprising alkoxy, polyoxyalkylene, alkylamido, hydroxyalkyl, and alkylester moieties, and combinations thereof. The compounds contain at least one hydrophilic moiety within 4, preferably within 3, carbon atoms (inclusive) of the quaternary nitrogen or cationic amino nitrogen. Additionally, carbon atoms that are part of a hydrophilic moiety, e.g., carbon atoms in a hydrophilic polyoxyalkylene (e.g.,—$CH_2$—$CH_2$—O—), that are adjacent to other hydrophilic moieties are not counted when determining the number of hydrophilic moieties within 4, or preferably 3, carbon atoms of the cationic nitrogen. In general, the alkyl portion of any hydrophilic moiety is preferably a $C_1$–$C_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methyl ester, ethyl ester, propyl ester, or mixtures thereof, as nonionic hydrophile moieties. The compounds must be positively charged at the pH of the shampoo compositions. Generally, the pH of the shampoo compositions will be less than about 10, typically from about 3 to about 9.

Among the cationic surfactants useful herein are those of the general formula

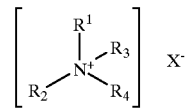

wherein $R_1$, $R_2$, $R_3$, and $R_4$ independently represent hydrocarbyl chains of from about 1 to about 30 carbon atoms, or hydrocarbyl chain having from about 1 to about 30 carbon atoms and optionally containing one or more aromatic, ether, ester, amido, or amino moieties present as substituients or as linkages in the hydrocarbyl chain, where at least one of the $R_1$–$R_4$ groups is optionally substituted with at least one or more hydrophilic moieties independently selected from alkoxy (preferably $C_1$–$C_3$ alkoxy), polyoxyalkylene (preferably $C_1$–$C_3$ polyoxyalkylene), alkylamido, hydroxyalkyl, and alkylester; and X is a soluble salt forming anion.

Preferably X is selected from the group comprising halogens (especially chlorine), acetate, phosphate, nitrate, sulfonate, and alkyl sulfate radicals.

Preferably, the cationic conditioning surfactant contains from about 2 to about 10 nonionic hydrophile moieties located within the above stated ranges.

For purposes herein, each hydrophilic amido, alkoxy, hydroxyalkyl, alkylester, alkylamido or other unit is considered to be a distinct nonionic hydrophile moiety.

Preferred cationic surfactants include polyoxyethylene (2) stearyl methyl ammonium chloride, methyl bis-(hydrogenated tallowamidoethyl) 2-hydroxyethyl ammonium methyl sulfate, polyoxypropylene (9) diethyl methyl ammonium chloride, tripolyoxyethylene (total PEG-10) stearyl ammonium phosphate, bis-(N-hydroxyethyl-2-oleyl imidazolinium chloride) polyethylene glycol (1), and isododecylbenzyl triethanolammonium chloride.

Other ammonium quaternary and amino compounds include those of the above general formula in the form of ring structures formed by covalently linking two of $R_1$–$R_4$ groups. Examples include imidazolines, imidazoliniums, and pyridiniums, etc., wherein said compound has at least one nonionic hydrophile-containing radical as set forth above. Specific examples include 2-heptadecyl-4,5-dihydro-1 H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxoctadecyl)oxy]ethyl]amino]ethyl] pyridinium chloride.

Salts of primary, secondary and tertiary fatty amines are also preferred cationic surfactant materials. The alkyl groups of such amines preferably have from about 1 to about 30 carbon atoms and must contain at least one, preferably about 2 to about 10, nonionic hydrophilic moieties selected from the group comprising alkoxy, polyoxyalkylene, alkylamido, hydroxyalkyl, and alkylester groups, and mixtures thereof. Secondary and tertiary amines are preferred, tertiary amines are particularly preferred. Specific examples of suitable amines include diethyl aminoethyl polyoxyethylene (5) laurate, coco-polyglyceryl (4) hydroxypropyl dihydroxy ethylamine and dihyroxyethyl tallowamine hydrochloride.

The pH of the present compositions is not generally critical and may be in the range of from about 2 to about 10, preferably from about 3 to about 9, more preferably from about 4 to about 8. Thus, it is believed that the pH does not affect the interaction of the cationic conditioning agent and the anionic polymer.

In a preferred embodiment of the present invention, the anionic polymer is present from about 0.001 percent to about 5.0 percent, based on the total weight of the hair care composition. In a more preferred embodiment of the present invention, the anionic polymer is present from about 0.3 percent to about 2.0 percent, based on the total weight of the hair care composition.

In general, the anionic polymer comprises a polymer with one or more carboxylic acid groups, one or more carboxylic acid alkali metal salt groups, one or more sulfate groups, one or more sulfonate groups and mixtures thereof. Thus, the anionic polymer is a polymer selected from, but not limited to, the group comprising polymeric condensation products of methyl vinyl ether and maleic anhydride and salts, half acid esters and half acid amides thereof, salts of the half acid ester and/or half amide ester of the copolymeric condensation products of methyl vinyl ether and maleic anhydride, sodium salts of terpolymers of octyl acrylamide, polymeric condensation products of acrylate esters and butylaminoethyl methacrylate, acrylic acid polymers cross-linked with a polyfunctional agent and mixtures thereof. The polyfunctional agent is an agent selected from, but not limited to, the group comprising a polyol, a polyamine, carboxymethyl cellulose and mixtures thereof.

Additionally, the anionic polymer member may contain at least one carboxylic acid group, or at least one sulfate group, or at least one sulfonate group, or a mixture thereof, and is the product of a radical polymerization reaction of an ethylenically unsaturated monomer.

The anionic polymers employed in the invention have molecular weights in excess of 50,000, and preferably in excess of 75,000. More preferably, the anionic polymers have molecular weights in excess of 200,000, and most preferably in excess of 500,000. The cationic surfactants suitable for use in the invention typically are of relatively low molecular weights. Thus, these cationic surfactants contribute only a small portion of the molecular weight of the molecule. In all aspects of the invention, it is critical that the anionic polymer has a molecular weight sufficient to form a complex with a molecular weight of at least about 100,000.

In a preferred embodiment of the present invention, the swellable polymer thickening agent is present from about 0.2 percent to about 3.0 percent, based on the total weight of the hair care composition. In a more preferred embodiment of the present invention, the swellable polymer thickening agent is present from about 0.2 percent to about 2.0 percent, based on the total weight of the hair care composition. The swellable polymer thickening agent is an agent selected from the group comprising methyl cellulose, ethyl cellulose, xanthan gum, gum arabic, gum karaya, guar gum, locust bean gum, ghatti gum, hydrolyzed starches, low molecular weight ethylene oxide polymers, low molecular weight propylene oxide polymers and mixtures thereof.

The optional ingredients in accordance with the present invention are selected from the group comprising anti-dandruff agents, fragrance oils, perfumes, coloring agents, dyes, sequestering agents, preservatives, pearlescent/suspending agents, thickeners, viscosity modifiers, pH adjusting agents, gelling agents, opacifying agents, foam stabilizing auxiliary surfactants, silicone oils, nonvolatile/nonionic silicone conditioning agents, vitamins, protein, sunscreen agents and mixtures thereof. This list of optional ingredients is not meant to be exclusive, and other optional components can be utilized.

These optional ingredients generally are used individually at a level of from about 0.001% to about 10%, most commonly from about 0.5 to about 5% by weight of the composition.

Suitable anti-dandruff agents are selected from the group comprising zinc pyrithione, selenium sulfide, sulfur, coal tar, zinc omadine, piroctone olamine and mixtures thereof.

Suitable preservatives are selected from the group comprising benzyl alcohol, methyl paraben, propyl paraben and imidazolidinyl urea.

Suitable thickeners and viscosity modifiers are selected from the group comprising diethanolamides of long chain fatty acids (e.g., PEG-3 lauramide), block polymers of ethylene oxide and propylene oxide such as Pluronic® F88 offered by BASF, Wyandotte, sodium chloride, sodium sulfate, ammonium xylene sulfonate, ethyl alcohol and polyhydridic alcohols such as, for example, propylene glycol and polyvinyl alcohol.

Suitable gelling agents include, for example, hydroxyethyl cellulose.

Suitable pH adjusting agents are selected from the group comprising citric acid, succinic acid, phosphoric acid, sodium hydroxide, sodium carbonate, etc.

Suitable sequestering agents include, for example, disodium ethylenediamine tetraacetate.

Suitable foam stabilizing auxiliary surfactants include, for example, amides, amine oxides, betaines, sultaines and $C_8$–$C_{18}$ fatty alcohols.

Amine oxides useful as foam stabilizing auxiliary surfactants in the present invention include long-chain amine oxides, i.e., those compounds having the general formula

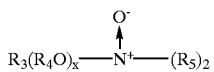

wherein
  $R_3$ is selected from an alkyl, hydroxyalkyl, acylamidopropyl and alkyl phenyl group, or mixtures thereof, containing from about 8–26 carbon atoms, preferably from about 8–16 carbon atoms;
  $R_4$ is an alkylene or hydroxyalkylene group containing from about 2–3 carbon atoms, preferably 2 carbon atoms, or mixtures thereof; x is from about 0–3, preferably 0; and
  each $R_5$ is an alkyl or hydroxyalkyl group containing from about 1–3, preferably from about 1–2 carbon atoms, or a polyethylene oxide group containing from about 1–3, preferably 1, ethylene oxide groups.

The $R_5$ groups can optionally be attached to each other, e.g., through an oxygen or nitrogen atom, to form a ring structure.

These foam stabilizing amine oxide auxiliary surfactants in particular include $C_{10}$–$C_{18}$ alkyl dimethyl amine oxides and $C_8$–$C_{12}$ alkoxy ethyl dihydroxyethyl amine oxides. Examples of such materials include dimethyloctylamine oxide, diethyldodecylamine oxide, bis-(2-hydroxyethyl) dodecylamine oxide, dimethyldodecylamine oxide, dodecylamidopropyl dimethylamine oxide and dimethyl-2-hydroxyoctadecylamine oxide. Preferred are $C_{10}$–$C_{18}$ alkyl dimethylamine oxide, and $C_{10}$–$C_{18}$ acylamido alkyl dimethylamine oxide.

Betaines

The betaines useful as foam stabilizing auxiliary surfactants in the present invention include compounds having the formula $R(R_1)_2N^+R_2COO^-$ wherein R is a $C_6$–$C_{18}$ hydrocarbyl group, preferably $C_{10}$–$C_{16}$ alkyl group, each $R_1$ is typically $C_1$–$C_3$, alkyl, preferably methyl, and $R_2$ is a $C_1$–$C_5$ hydrocarbyl group, preferably a $C_1$–$C_5$ alkylene group, more preferably a $C_1$–$C_2$ alkylene group. Examples of suitable betaines include coconut acylamidopropyldimethyl betaine; hexadecyl dimethyl betaine; $C_{12}$–$C_{14}$ acylamidopropylbetaine; $C_8$–$C_{14}$ acylamidohexyldiethyl betaine; 4-[$C_{14}$–$C_{16}$ acylmethylamidodiethylammonio]- 1-carboxybutane; $C_{16}$–$C_{18}$ acylamidododimethylbetaine; $C_{12}$–$C_{16}$ acylamidopentanediethylbetaine; $C_{12}$–$C_{16}$ acylmethylamidodimethylbetaine. Preferred betaines are $C_{12}$–$C_{18}$ dimethylamoniohexanoate and the $C_{10}$–$C_{18}$ acylamidopropane (or ethane) dimethyl (or diethyl) betaines.

Sultaines

The sultaines useful as foam stabilizing auxiliary surfactants in the present invention include compounds having the formula $R(R_1)_2N^+R_2SO_3^-$, wherein R is a $C_6$–$C_{18}$ hydrocarbyl group, preferably a $C_{10}$–$C_{16}$ alkyl group, more preferably a $C_{12}$–$C_{13}$ alkyl group; each $R_1$ is typically $C_1$–$C_3$ alkyl, preferably methyl and $R_2$ is a $C_1$–$C_6$ hydrocabyl group, preferably a $C_1$–$C_3$ alkylene or, preferably, hydroxyalkylene group. Examples of suitable sultaines are $C_{12}$–$C_{14}$ dihydroxyethylammino propane sulfonate, and $C_{16}$–$C_{18}$ dimethylammonio hexane sulfonate, with $C_{12}$–$C_{14}$ amido propyl ammonio-2-hydroxypropyl sultaine being preferred.

Optional Components

The auxiliary foam stabilizing surfactant may also be a fatty acid amide surfactant. Preferred amides are $C_8$–$C_{20}$ alkanol amides, monoethanolamides, diethanolamides and isopropanolamides. A particularly preferred amide is a mixture of myristic monoethaolamide and lauric monoethanolamide. This preferred amide is sold by Stepan Company, Northfield, Ill. as Ninol® LMP.

Optional non-volatile, nonionic silicone conditioning agents suitable for the present invention are selected from the group comprising polyalkyl siloxanes, polyaryl siloxanes, polyalkylaryl siloxanes, polyether siloxane copolymers and mixtures thereof. However, it should also be noted that any silicone fluid having hair conditioning properties may used as an optional ingredient in the present Compositions. The nonvolatile polyalkyl siloxane fluids that may be used include, for example, polydimethylsiloxanes, available, for example, from General Electric Company as SF 1075 methyl phenyl fluid or from Dow Corning as 556 Cosmetic Grade Fluid. The polyether siloxane copolymers that may be used include, for example, a polypropylene oxide modified dimethylpolysiloxane (E.g., Dow Corning DC-1248) although ethylene oxide or mixtures of ethylene oxide and propylene oxide may also be used.

Optional silicone fluids hereof also include polyalkyl or polyaryl siloxanes with the following general formula:

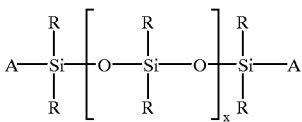

wherein R is alkyl or aryl, and x is an integer form about 7 to about 8,000. "A" represents groups which block the ends of the silicone chains.

The alkyl or aryl groups substituted on the siloxane chain or at the ends of the siloxane chains (A) may have any structure as long as the resulting silicones remain fluid at room temperature, are hydrophobic, are neither irritating, toxic nor otherwise harmful when applied to the hair, are compatible with the other components of the present compositions, are chemically stable under normal use and storage conditions, and are capable of being optionally deposited on and of optionally conditioning the hair.

Suitable A groups include methyl, methoxy, ethoxy, propoxy, and aryloxy. The two R groups on the silicone atom may represent the same or different groups. Preferably, the two R groups represent the same group. Suitable R groups include, for example, methyl, ethyl, propyl, phenyl, methylphenyl and phenylmethyl. The preferred silicones are polydiemethyl siloxane, polydiethyl siloxane and polymethylphenyl siloxane. Polydiemethyl siloxane is especially preferred.

The optional pearlescent/suspending agents suitable for use in the present invention include any of several long chain acyl derivative materials or mixtures of such materials, such as long chain acyl derivatives, long chain amine oxides, and mixtures thereof, wherein such suspending/pearlescent agents are present in the composition in crystalline form. These pearlescent/suspending agents are described in U.S. Pat. No. 4,741,855, Grote and Russell, issued May 3, 1988, the disclosure of which is incorporated herein by reference in its entirety. Included are ethylene glycol esters of fatty acids having from about 16 to about 22 carbon atoms. Preferred are the ethylene glycol stearates, both mono- and distearate, but particularly the distearate containing less than about 7% of the monostearate. Other suspending agents found useful are alkanolamides, preferably with about 16 to about 18 carbon atoms. Preferred alkanolamides are stearic monoethanolamide, stearic diethanolamine, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain ester of long chain alkanol amides (e.g., stearamide DEA distearate, stearamide MEA stearate).

Additional optional pearlescent/suspending agents suitable for use in the present invention are alkyl ($C_{18}$–$C_{22}$) dimethyl amine oxides, such as stearyl dimethyl amine oxide. If the compositions contain an amine oxide or a long chain acyl derivative as a surfactant the pearlescent/suspending function could also be provided by such surfactant and additional pearlescent/suspending agents may not be needed.

Further optional pearlescent/suspending agents that can be used are long chain acyl derivatives, including, for example, N,N-dihydroxycarbyl amido benzoic acid and soluble thereof (e.g., Na and K salts), particularly N,N-di (hydrogenated) $C_{16}$, $C_{18}$ and tallow amido benzoic acid species of this family, which are commercially available from Stepan Company (Northfield, Ill., USA).

Another type of pearlescent/suspending agent which can be used in the present invention is xanthan gum. Xanthan gum is well known to those skilled in the art. For example, hair care compositions utilizing xanthan gum as a pearlescent/suspending agent for the silicone hair conditioning component are described in U.S. Pat. No. 4,788,066, Bolich and Williams, issued Nov. 29, 1988, the disclosure of which is incorporated herein by reference in its entirety. See also, Whistler, Roy L. Editor Industrial Gums—Polysaccharides and Their Derivatives, New York: Academic Press, 1973. Xanthan gum is commercially available from Kelco, a division of Merck & Co., Inc. as Keltrol.

Combinations of long chain acyl derivatives and xanthan gum are disclosed as pearlescent/suspending agents for silicone hair conditioners in U.S. Pat. No. 4,704,272, Oh et al., issued Nov. 3, 1987, both of which are incorporated herein by referencein their entirety, and may also be used in the present compositions. Gel formulations have high levels of pearlescent/suspending agents relative to pourable, liquid formulations which used as the primary means of imparting the gel-like viscosity to the composition.

Optional gelling agents suitable for use in the present invention include, for example, hydroxy ethylcellulose.

While compositions of the present invention have been disclosed for used in hair care applications, other applications for these compositions are possible. The compositions of the present invention may be useable in or as liquid dish washing compositions, hand soaps, multi-purpose cleaners, body washes, laundry detergent compositions, textile treatment compositions, etc.

All documents, e.g., patents and journal articles, cited above or below are hereby incorporated by reference in their entirety.

In the following examples, all amounts are stated in percent by weight of active material unless indicated otherwise. One skilled in the art will recognize that modifications may be made in the present invention without deviating from the spirit or scope of the invention. The invention is illustrated further by the following examples which are not to be construed as limiting the invention or scope of the specific procedures or compositions described herein.

The definitions and CTFA designations used in the present invention are as follows:

| | |
|---|---|
| Methocel J75MS | hydroxypropyl methylcellulose |
| Keltrol RD | xanthan gum |
| Gantrez AN179 | poly(methyl vinyl ether/maleic anhydride) (PVM/MA) copolymer |
| Ammonyx CETAC | cetyl trimethyl ammonium chloride |
| Amphosol SB or SBG | cocoamidopropyl hydroxysultaine |
| Amphosol CA | cocoamidopropyl betaine |
| KESSCO EGDS | ethyleneglycol distearate |
| KESSCO EGMS | ethyleneglycol monostearate |
| Glydant | dimethyl dimethyl (DMDM) hydantoin |
| Ammonyx 4 | stearylalkonium chloride |
| Ammonyx GA70 PG | dipalmitoylethyl hydroxyethylammonium methosulfate |
| Ammonyx D34 | dicetyldimonium chloride |
| Ammonyx KP | olealkonium chloride |
| Amphomer | octylacrylamide/acrylates/butylaminoethyl methacrylates copolymer |
| Carbopol ETD2001 | carbomer 2001 |
| Luvimer 100P | acrylates copolymer |
| Plantaran 2000 | decyl polyglucoside |
| Ammonyx LO | lauramine oxide |
| Stepanol AM | ammonium lauryl sulfate |
| Lexamine S-13 | stearamidopropyl dimethylamine |
| Armeen 18D | stearamine |
| Armeen OD | oleamine |
| Armeen 2HT | dihydrogenated tallow amine |
| Ninol LMP | lauric/myristic monoethanolamide |

-continued

| | |
|---|---|
| LA 150M | C12 with 14.6 moles ethoxylated methyl ester (Lion Corp., Japan) |
| LC 110M | C12 with 10.8 moles ethoxylated methyl ester (Lion Corp., Japan) |
| ACV-4043 copolymer | stabilized methyl vinyl ether/maleic acid (anhydride) or salt co-polymer, having a molecular weight of 2,000,000 ± 500,000 (International Specialty Products) |
| Neodol 91-8 | $C_9$ and $C_{11}$ ethoxylated fatty alcohol with 8 moles ethylene oxide (Shell Chemical Company) |
| DDABDT | dodecyl dimethylaminobenzezmide propyldimethylammonium tosylate (ISP) |

Example 1

Method of Preparation #1 (Formulations 2 and 3)

A suitable vessel equipped with a means for mixing, a means for heating, and a means for cooling is sequentially charged with deionized water and Keltrol RD. These ingredients are mixed to produce a homogeneous dispersion. The contents of the vessel are heated to 70° C. The combined ingredients are mixed to produce a homogeneous solution. Next, Gantrez AN179 solution is added followed by the addition of the AMMONYX CETAC, AMPHOSOL SB or SBG, AMPHOSOL CA, KESSCO EGDS, or KESSCO EGMS. The resulting combination of ingredients is mixed for 10–15 minutes. The mixture is cooled to 40° C. and the Glydant added. The pH of the mixture is adjusted to 4.0–7.5 and mixture cooled to ambient temperature.

Preferred Method of Preparation #2
(Formulation 1)

A suitable vessel equipped with a means for mixing and a means for cooling is sequentially charged with deionized water and Keltrol RD. These ingredients are mixed to produce a homogeneous dispersion. The combined ingredients are mixed to produce a homogeneous solution. Next, Gantrez AN179 solution is added followed by the addition of the AMPHOSOL SB or SBG, AMPHOSOL CA, and AMMONYX CETAC. The resulting combination of ingredients is mixed for 10–15 minutes and the Glydant is added. The pH of the final mixture is adjusted to 4.0–7.5.

Preferred Method of Preparation #3

A suitable vessel equipped with a means for mixing, a means for heating, and a means for cooling is sequentially charged with deionized water and Keltrol RD. These ingredients are mixed to produce a homogeneous dispersion. The contents of the vessel are heated to 70° C. The combined ingredients are mixed to produce a homogeneous solution. Next, Gantrez AN179 solution is added followed by the addition of the AMPHOSOL SB or SBG and AMPHOSOL CA, AMMONYX CETAC, KESSCO EGDS or KESSCO EGMS. The resulting combination of ingredients is mixed for 10–15 minutes. The mixture is cooled to ambient temperature and the Glydant added. The pH of the final mixture is adjusted to 4.0–6.5.

Example 2

Preparation of Gantrez AN179 Solution

A suitable vessel equipped with a means for mixing, a means for heating, and a means for cooling is charged with deionized water and heated to 80° C. Gantrez AN179 powder is added and the resulting mixture agitated for 30 minutes or until a clear, homogeneous solution is formed. The mixtures is finally cooled to ambient temperature.

Isolation of Styling/Conditioning Agents

A suitable vessel equipped with a means for mixing is sequentially charged with 400 ml of water, 5 g of formulation 1 (other formulations may be substituted) and the resulting mixture stirred for 2 minutes. During this period of time, the fibrils are released into the solution and were be isolated by filtration using filter paper.

Example 3

Method for Re-Styling the Hair #1

Hair that has been previously treated with a hair care composition of the present invention (i.e. formulations 1, 2 and 3) is wetted with water. The hair is combed and allowed to air dry or is dried with a mechanical means.

Method for Re-Styling the Hair #2

Hair that has been previously treated with a hair care composition of the present invention (i.e. formulations 1, 2 and 3) is wetted with water. The hair is combed, set on rollers, allowed to air dry or is dried with a mechanical means, the rollers are removed and the hair is combed out to achieve the desired hair style.

Example 4

The following formulations were prepared according to the according to the methods set forth above.

|  | FORMULATION | | |
| --- | --- | --- | --- |
|  | 1 wt. % (as is) | 2 wt. % (as is) | 3 wt. % (as is) |
| 1. D.I. Water | Q.S. to 100.0 | Q.S. to 100.00 | Q.S. to 100.00 |
| 2. Keltrol RD | 1.0 | 1.0 | 1.0 |
| 3. Gantrez AN179 (5%) | 8.00 | 8.00 | 8.00 |
| 4. AMMONYX ® CETAC (30%) | 5.80 | 5.80 | 5.80 |
| 5. AMPHOSOL ® SB or SBG (50%) | 24.00 | 24.00 | 24.00 |
| 6. AMPHOSOL ® CA (30%) | 10.00 | 10.00 | 10.00 |
| 7. KESSCO ® EGDS | — | 2.00 | — |
| 8. KESSCO ® EGMS | — | — | 2.00 |
| 9. Glydant | 0.25 | 0.25 | 0.25 |
| Conditioning Effect on hair | Excellent | Excellent | Excellent |
| Styling/Setting/Body/ Stiffness on hair | Excellent | Excellent | Excellent |
| pH | 5.6 | 5.6 | 5.6 |
| Appearance | Translucent | Opaque | Pearlescent opaque |
| Dispersion type | Isotropic liquid | Anisotropic liquid | Isotropic liquid |

|  | FORMULATION | | | |
| --- | --- | --- | --- | --- |
|  | 4 wt. % (as is) | 5 wt. % (as is) | 6 wt. % (as is) | 7 wt. % (as is) |
| 1. D.I. Water | Q.S. to 100.0 | Q.S. to 100.0 | Q.S. to 100.0 | Q.S. to 100.0 |
| 2. Methocel J75MS | 0.75 | 0.75 | 0.75 | 0.75 |
| 3. Keltrol RD | 0.40 | 0.40 | 0.40 | 0.40 |
| 4. NaOH 50% | 0.05 | 0.05 | 0.05 | 0.05 |
| 5. Gantrez AN179 (5%) | 8.00 | 8.00 | 8.00 | 8.00 |
| 6. AMMONYX ® 4 (18%) | 9.70 | — | — | — |
| 7. AMMONYX ® GA70 PG (70%) | — | 2.50 | — | — |
| 8. AMMONYX ® D34 (68%) | — | — | 2.56 | — |
| 9. AMMONYX ® KP (50%) | — | — | — | 3.48 |
| 10. AMPHOSOL ® SB or SBG (50%) | 24.00 | 24.00 | 24.00 | 24.00 |
| 11. AMPHOSOL ® CA (30%) | 10.00 | 10.00 | 10.00 | 10.00 |
| 10. KESSCO ® EGMS | 2.00 | 2.00 | 2.00 | 2.00 |
| 11. Glydant | 0.25 | 0.25 | 0.25 | 0.25 |
| Conditioning Effect on hair | Excellent | Excellent | Excellent | Excellent |
| Styling/Setting/Body/ Stiffness on hair | Excellent | Excellent | Excellent | Excellent |
| pH | 5.6 | 4.0 | 5.6 | 5.6 |
| Appearance | Opaque Pearlescent | Opaque Pearlescent | Opaque Pearlescent | Opaque Pearlescent |
| Dispersion type | Isotropic liquid | Isotropic liquid | Isotropic liquid | Isotropic liquid |

|  | FORMULATION | | | |
| --- | --- | --- | --- | --- |
|  | 8 wt. % (as is) | 9 wt. % (as is) | 10 wt. % (as is) | 11 wt. % (as is) |
| 1. D.I. Water | Q.S. to 100.0 | Q.S. to 100.0 | Q.S. to 100.0 | Q.S. to 100.0 |
| 2. Methocel J75MS | 0.75 | 0.75 | 0.75 | 0.75 |
| 3. Keltrol RD | 0.40 | 0.40 | 0.40 | 0.40 |
| 4. NaOH 50% | 0.05 | 0.05 | 0.05 | 0.05 |
| 5. Gantrez AN179 (5%) | 8.00 | 8.00 | 8.00 | 8.00 |
| 6. Lexamine S-13 | 1.75 | — | — | — |
| 7. Armeen 18D | — | 1.75 | — | — |
| 8. Armeen OD | — | — | 1.75 | — |
| 9. Armeen 2HT | — | — | — | 1.75 |
| 10. AMPHOSOL ® SB or SBG (50%) | 24.00 | 24.00 | 24.00 | 24.00 |
| 11. AMPHOSOL ® CA (30%) | 10.00 | 10.00 | 10.00 | 10.00 |
| 10. KESSCO ® EGMS | 2.00 | 2.00 | 2.00 | 2.00 |
| 11. Glydant | 0.25 | 0.25 | 0.25 | 0.25 |
| Conditioning Effect on hair | Excellent | Excellent | Excellent | Excellent |
| Styling/Setting/Body/ Stiffness on hair | Excellent | Excellent | Good | Good |
| pH | 5.6 | 5.6 | 5.6 | 5.6 |
| Appearance | Opaque Pearlescent | Opaque Pearlescent | Opaque Pearlescent | Opaque Pearlescent |
| Dispersion type | Isotropic liquid | Isotropic liquid | Isotropic liquid | Isotropic liquid |

| | FORMULATION (all components by Weight %, as is) | | | | |
|---|---|---|---|---|---|
| | 12 | 13 | 14) | 15 | 16 |
| 1. D.I. Water | Q.S. to 100.0 | Q.S. to 100.0 | Q.S. to 100.0 | Q.S. to 100.0 | Q.S. to 100.0 |
| 2. Methocel 375MS | 0.75 | 0.75 | 0.75 | 0.75 | 0.75 |
| 3. Keltrol RD | 0.40 | 0.40 | 0.40 | 0.40 | 0.40 |
| 4. NaOH 50% | 0.05 | 0.05 | 0.05 | 0.05 | 0.05 |
| 5. Gantrez AN119 (5%) | 8.00 | — | — | — | — |
| 6. Gantrez AN903 (5%) | — | 8.00 | — | — | — |
| 7. Amphomer (5%) | — | — | 8.00 | — | — |
| 8. Carbopol ETD2001 (2%) | — | — | — | 20.00 | — |
| 9. Luvimer 100P (5%) | — | — | — | — | 8.00 |
| 10. AMMONYX ® CETAC (30%) | 5.80 | 5.80 | 5.80 | 5.80 | 5.80 |
| 11. AMPHOSOL ® SB or SBG (50%) | 24.00 | 24.00 | 24.00 | 24.00 | 24.00 |
| 12. AMPHOSOL ® CA (30%) | 10.00 | 10.00 | 10.00 | 10.00 | 10.00 |
| 13. KESSCO ® EGDS | 2.00 | 2.00 | 2.00 | 2.00 | 2.00 |
| 14. Glydant | 0.25 | 0.25 | 0.25 | 0.25 | 0.25 |
| Conditioning Effect on hair | Excellent | Excellent | Good | Good | Good |
| Styling/Setting/Body/Stiffness on hair | Excellent | Excellent | Good | Good | Fair |
| pH | 5.6 | 5.6 | 5.6 | 5.6 | 5.6 |
| Appearance | Opaque Pearlescent | Opaque Pearlescent | Opaque Pearlescent | Opaque Pearlescent | Opaque Pearlescent |

| | FORMULATION (all components by Weight %, as is) | | | |
|---|---|---|---|---|
| | 17* | 18 | 19 | 20 |
| 1. D.I. Water | Q.S. to 100.0 | Q.S. to 100.0 | Q.S. to 100.0 | Q.S. to 100.0 |
| 2. Keltrol RD | 1.0 | 1.0 | 1.0 | 1.0 |
| 3. AMPHOSOL ® SB (50%) | 24.0 | 24.0 | 24.0 | 24.0 |
| 4. AMPHOSOL ® CA (30%) | 10.0 | 10.0 | 10.0 | 10.0 |
| 5. Gantrez AN179 (5%) | — | 5.00 | 8.00 | 8.00 |
| 6. AMMONYX ® CETAC (30%) | — | 5.0 | 6.67 | 3.33 |
| Molar ratio of Gantrez AN179 to AMMONYX GA70 PG | — | 2:1 | 2.7:1 | 3.1 |
| Conditioning Effect on hair | Very poor | Excellent | Excellent | Good |
| Styling/Setting/Body/Stiffness on hair | Very poor | Excellent | Excellent | Good |
| pH | 4.5 | 4.5 | 4.5 | 4.5 |
| Appearance | Translucent | Translucent | Translucent | Translucent |

*No styling/conditioning complex

| | FORMULATION | | | | |
|---|---|---|---|---|---|
| | 21 wt. % (as is) | 22 wt. % (as is) | 23 wt. % (as is) | 24 wt. % (as is) | 25 wt. % (as is) |
| 1. D.I. Water | Q.S. to 100.0 | Q.S. to 100.0 | Q.S. to 100.0 | Q.S. to 100.0 | Q.S. to 100.0 |
| 2. Methocel J75MS | 0.75 | 0.75 | 0.75 | 0.75 | 0.75 |
| 3. Keltrol RD | 0.40 | 0.40 | 0.40 | 0.40 | 0.40 |
| 4. NaOH 50% | 0.05 | 0.05 | 0.05 | 0.05 | 0.05 |
| 5. Gantrez AN179 (5%) | 1.0 | 2.0 | 3.0 | 6.0 | 8.0 |
| 6. AMMONYX ® CETAC (30%) | 5.80 | 5.80 | 5.80 | 5.80 | 5.80 |
| 7. AMPHOSOL ® SB or SBG (50%) | 24.00 | 24.00 | 24.00 | 24.00 | 24.00 |
| 8. AMPHOSOL ® CA (30%) | 10.00 | 10.00 | 10.00 | 10.00 | 10.00 |
| 9. KESSCO ® EGDS | 2.00 | 2.00 | 2.00 | 2.00 | 2.00 |
| 10. Glydant | 0.25 | 0.25 | 0.25 | 0.25 | 0.25 |
| Conditioning Effect on hair | Excellent | Excellent | Excellent | Excellent | Excellent |
| Styling/Setting/Body/Stiffness on hair | Poor | Fair | Good | VERY Good | Excellent |
| pH | 5.6 | 5.6 | 5.6 | 5.6 | 5.6 |
| Appearance | Opaque Pearlescent | Opaque Pearlescent | Opaque Pearlescent | Opaque Pearlescent | Opaque Pearlescent |

| FORMULATION (all components by Weight %, as is) | | | | | | |
|---|---|---|---|---|---|---|
| | 26 | 27 | 28 | 29 | 30 | 31 |
| 1. D.I. Water | Q.S. to 100.0 | | | | | |
| 2. Methocel J75MS | 0.75 | 0.75 | 0.75 | 0.75 | 0.75 | 0.75 |
| 3. Keltrol RD | 0.40 | 0.40 | 0.40 | 0.40 | 0.40 | 0.40 |
| 4. NaOH 50% | 0.05 | 0.05 | 0.05 | 0.05 | 0.05 | 0.05 |
| 5. Gantrez AN179 (5%) | 8.00 | 8.00 | 8.00 | 8.00 | 8.00 | 8.00 |
| 6. AMMONYX ® CETAC (30%) | 5.80 | 5.80 | 5.80 | 5.80 | 5.80 | 5.80 |
| 7. AMPHOSOL ® SB or SBG (50%) | 24.00 | 24.00 | — | — | 24.00 | — |
| 8. Plantaran 2000 (50%) | 10.00 | — | — | 30.0 | — | — |
| 9. AMMONYX ® LO (30%) | — | 3.33 | — | — | 10.0 | — |
| 10. AMPHOSOL ® CA (30%) | — | 10.00 | — | — | — | 50.0 |
| 11. STEPANOL ® AM (29%) | — | — | 48.00 | — | — | — |
| 12. NINOL ® LMP | — | — | 3.00 | — | — | — |
| 13. KESSCO ® EGMS | 2.00 | 2.00 | 2.00 | 2.00 | 2.00 | 2.00 |
| 14. Glydant | 0.25 | 0.25 | 0.25 | 0.25 | 0.25 | 0.25 |
| Conditioning Effect on hair | Excellent | Very Good | Very poor | Excellent | Excellent | Excellent |
| Styling/Setting/Body/Stiffness on hair | Excellent | Very Good | Very poor | Excellent | Poor | Excellent |
| pH | 5.6 | 5.6 | 5.6 | 5.6 | 5.6 | 5.6 |
| Appearance | Opaque Pearlescent | Opaque Pearlescent | Opaque Pearlescent | Opaque Pearlescent | Opaque Pearlescent | Opaque Pearlescent |

| FORMULATION | | | | |
|---|---|---|---|---|
| | 32 wt. % (as is) | 33 wt. % (as is) | 34 wt. % (as is) | 35 wt. % (as is) |
| 1. D.I. Water | Q.S. to 100.0 | Q.S. to 100.0 | Q.S. to 100.0 | Q.S. to 100.0 |
| 2. Methocel J75MS | 0.75 | 0.75 | — | 0.75 |
| 3. Keltrol RD | 0.40 | 0.40 | 1.0 | 0.40 |
| 4. NaOH 50% | 0.05 | 0.05 | — | 0.05 |
| 5. Gantrez AN179 (5%) | 8.00 | 8.00 | 8.0 | 8.00 |
| 6. AMMONYX ® CETAC (30%) | 5.80 | 5.80 | 5.8 | 5.80 |
| 7. AMPHOSOL ® SB or SBG (50%) | 30.00 | 30.00 | 10.0 | 30.00 |
| 8. Plantaran 2000 (50%) | — | — | 10.0 | — |
| 9. AMPHOSOL ® CA (30%) | 10.00 | 10.00 | — | 10.00 |
| 10. AMMONYX ® LO (30%) | — | — | 10.0 | — |
| 9. KESSCO ® EGDS | 2.00 | 2.00 | 2.0 | — |
| 10. Silicone Gum/Silicone fluid (350 cps) 65:35 ratio | 1.00 | — | — | 1.00 |
| 11. Zinc Pyrithione (48%) | — | 2.10 | — | — |
| 12. STEPAN TAB-2 ®/SAB-2 | — | — | — | 3.5 |
| 13. Glydant | 0.25 | 0.25 | 0.25 | 0.25 |
| Conditioning Effect on hair | Excellent | Excellent | Excellent | Excellent |
| Styling/Setting/Body/Stiffness on hair | Excellent | Excellent | Excellent | Excellent |
| pH | 5.6 | 5.6 | 7.0 | 5.6 |
| Appearance | Opaque Pearlescent | Opaque | Opaque Pearlescent | Opaque |

| Formulation | | |
|---|---|---|
| | 36 Wt. % (as is) | 37 Wt. % (as is) |
| 1. D.I. Water | Q.S. to 100.0 | Q.S. to 100.0 |
| 2. Keltrol RD | 1.0 | 1.0 |
| 3. AMPHOSOL ® SB (50%) | 30.0 | 30.0 |
| 4. AMPHOSOL ® CA (30%) | 16.7 | 16.7 |
| 5. Gantrez AN179 (5%) | 8.0 | 8.0 |
| 6. Lexein QX 3000 (30%) | — | 5.8 |
| 7. DDABDT | 1.75 | — |
| 8. Glydant | 0.25 | 0.25 |
| Conditioning Effect on hair | Excellent | Fair |
| Styling/Setting/Body/Stiffness on hair | Excellent | Fair |
| pH | 5.2 | 5.2 |
| Appearance | Clear | Clear |

| FORMULATION | | | |
|---|---|---|---|
| | 38 wt. % (as is) | 39 wt. % (as is) | 40 wt. % (as is) |
| 1. D.I. Water | Q.S. to 100.0 | Q.S. to 100.0 | Q.S. to 100.0 |
| 2. Keltrol RD | 1.0 | 1.0 | 1.0 |
| 3. LA 150M (92%) | 8.97 | — | 8.97 |
| 4. LC 110M (100%) | — | 8.25 | — |
| 5. AMPHOSOL ® CA (30%) | 14.2 | 14.2 | 14.2 |
| 6. NINOL LMP | 2.5 | 2.5 | 2.5 |
| 7. Gantrez AN179 (5%) | 8.0 | 8.0 | — |
| 8. NaOH (50%) | 0.05 | 0.05 | 0.5 |
| 9. AMMONYX ® CETAC (30%) | 5.8 | 5.8 | 5.8 |
| 10. KESSCO ® EGDS | 2.00 | — | 2.0 |

-continued

| | FORMULATION | | |
|---|---|---|---|
| | 38 wt. % (as is) | 39 wt. % (as is) | 40 wt. % (as is) |
| 11. Glydant | 0.25 | 0.25 | 0.25 |
| Conditioning Effect on hair | Excellent | Excellent | Poor |
| Styling/Setting/Body/Stiffness on hair | Excellent | Excellent | Poor |
| pH | 5.6 | 5.6 | 7.0 |
| Appearance | Opaque Pearlescent | Clear | Opaque Pearlescent |
| Phase Type | Isotropic Liquid | Isotropic Liquid | Isotropic Liquid |

| | FORMULATION (all components by Weight %, as is) | | | | |
|---|---|---|---|---|---|
| | 41 | 42 | 43 | 44 | 45 |
| 1. D.I. Water | | | Q.S. to 100.0 | | |
| 2. AMPHOSOL ® SB (50%) | 30 | 30 | 30 | 30 | — |
| 3. Keltrol RD | 1.0 | 1.0 | 1.0 | 1.0 | 1.0 |
| 4. AMPHOSOL ® CA (30%) | 16.7 | 16.7 | 16.7 | 16.7 | 66.5 |
| 5. Gantrez AN179(5%) | — | 8.0 | — | 8.0 | 8.0 |
| 6. AMMONYX ® CETAC (30%) | — | — | 5.8 | 5.8 | 5.8 |
| Conditioning Effect on hair | Very poor | Very poor | Excellent | Excellent | Excellent |
| Styling/Setting/Body/Stiffness on hair | Poor | Poor | Poor | Excellent | Excellent |
| CMC (mg/l) | 80 | 60 | 80 | 60 | 60 |
| Surface Tension at CMC (mN/M) | 32 | 35 | 30.4 | 29.0 | 28.8 |
| Dilution in DI water (6 g/100 ml) | Clear | Clear | Clear with fibrils* | Clear with fibrils** | Clear with fibrils* |

*Agglomerated; **Non-agglomerated

As can be seen, several of the formulations exhibit low critical micelle concentration (CMC), as well as very low surface tension at the CMC. These characteristics are desirable in hair care compositions to impart excellent conditioning and styling benefits to the hair. Formulation #44 and formulation #45 contain cationic surfactants, anionic polymers, have critical micelle concentrations of about 60 mg/l, have surface tensions at the CMC of about 29 mN/m and impart excellent conditioning and styling properties to the hair. In contrast, formulation 42 and formulation 43 contain only anionic styling polymer or cationic surfactant. These formulations have a CMC of about 60 mg/l and 80 mg/l, respectively, and have surface tensions at the CMC's of about 35 nM/m and 30.5 mN/m, respectively. These formulations do not fulfill the requirements of low surface tension and low CMC, and as a result, do not impart both conditioning and styling properties to the hair. However, because formulation #43 shows very low surface tension, it

| | FORMULATION (all components by Weight %, as is) | | | | | |
|---|---|---|---|---|---|---|
| | 46 | 47 | 48 | 49 | 50 | 51 |
| 1. D.I. Water | Q.S. to 100.0 | Q.S. to 100.0 | Q.S. to 100.0 | Q.S. to 100.0 | Q.S. to 100.0 | Q.S. to 100.0 |
| 2. Keldrol RD | 0.5 | 0.5 | 0.8 | 0.8 | 0.5 | 0.5 |
| 3. Neodol 91-8 | 5.0 | 5.0 | 5.0 | 5.0 | 5.0 | 5.0 |
| 4. AMPHOSOL ® CA (30%) | 25.0 | 25.0 | 25.0 | 25.0 | 25.0 | 25.0 |
| 5. Ninol LMP | 2.5 | 2.5 | 2.5 | 2.5 | 2.5 | 2.5 |
| 6. Gantrez AN179 (5%) | 12.0 | 12.0 | — | — | — | 12.0 |
| 7. NaOH (50%) | Q.S. | Q.S. | — | — | Q.S. | Q.S. |
| 8. AMMONYX ® CETAC (30%) | 5.8 | 5.8 | 5.8 | 5.8 | — | — |
| 9. KESSCO ® EGDS | — | 2.0 | — | 1.5 | — | — |
| 10. Glydant | 0.25 | 0.25 | 0.25 | 0.25 | 0.25 | 0.25 |
| Conditioning Effect on hair | Excellent | Excellent | Excellent | Excellent | Very poor | Very poor |
| Styling/Setting/Body/Stiffness on hair | Excellent | Excellent | Poor | Poor | Very poor | Very poor |
| pH | 5.5 | 7.2 | 5.5 | 7.2 | 5.5 | 5.5 |
| Appearance | Clear Liquid | Opaque/Pearlescent Liquid | Clear Liquid | Opaque/Pearlescent Liquid | Clear Liquid | Clear Liquid |
| Phase Type | Isotropic Liquid | Isotropic Liquid | Isotropic Liquid | Isotropic Liquid | Isotropic Liquid | Isotropic Liquid | does impart excellent conditioning benefits to the hair, but no styling properties.

Example 5

The Use of Pre-Formed Styling Agents

A pre-formed anionic polymer/cationic surfactant (Gantrez AN178—Ammonyx CETAC) complex may be added to an non-ionic/amphoteric shampoo base to achieve desired cleaning, conditioning, and styling properties. An anionic polymer/cationic surfactant complex is formed according to Formulation # 54.

Formulation #54

| Ingredient | Weight % |
| --- | --- |
| 1. Deionized Water | 84.2 |
| 2. Gantrez AN179 (5%) | 10.0 |
| 3. Na OH (50%) | Q.S. To pH 5.8 |
| 4. Ammonyx CETAC (30%) | 5.8 |

A suitable vessel equipped with a means for mixing and heating is charged with ingredients 1 and 2 added and the resulting mixture agitated. The pH of the mixture is adjusted with ingredient 3 to a pH of about 5.8. Ingredient 4 is slowly added which results in the formation of the desired complex as a thick paste. The water is then substantially removed from paste by evaporation.

A three-in-one styling/conditioning shampoo is prepared utilizing the complex prepared according to Formulation 54 as shown below in Formulation # 55.

Formulation #55

| Ingredient | Weight % |
| --- | --- |
| 1. Deionized Water | 64.5 |
| 2. BIO-SOFT FF600 | 5.0 |
| 3. AMPHOSOL CA (30%) | 25.0 |
| 4. NINOL 55LL | 2.5 |
| 5. Complex Form. #54 | 3.0 |
| 6. Na OH 50% | Q.S. to pH 5.8 |

A suitable vessel equipped with a means for mixing and heating is charged with ingredients 1 through 4 at ambient temperature. The resulting mixture is heated to 140° F. and ingredient 5 is added; the resulting slurry is agitated until homogenous. The resulting product is a clear isotropic liquid. The normally insoluble styling/conditioning agent prepared in Formulation 54 readily dissociates into the individual complex components, i.e. the cationic surfactant and the anionic polymer, when added into a non-ionic/amphoteric surfactant base.

Approximately 6 grams of Formulation # 55 are diluted in deionized water. The styling/conditioning agent in the form of macrofibrils is present and readily falls out of solution. Formulation #55 showed excellent foaming, conditioning, and styling properties on De Meo Brothers European natural brown hair.

Comparative Example 1: The Use of Anionic Surfactants

Several attempts were made in the use of anionic surfactants in the present invention in place of the aforementioned nonionic surfactants or in combination with the nonionic surfactants. Example formulations 52 and 53 are shown below as examples which utilize an alkyl ether carboxylate (AEC; derived from Neodol® 23-6, Shell) and coconut fatty acid potassium soap (from McIntyre) respectively.

Formulations 52 and 53 were evaluated as follows. A 6 g portion of each sample was added to 100 ml of deionized water. Neither sample produced styling/conditioning fibrils upon dilution as desired. Each formulation was tested on virgin brown hair and both formulations produced very poor styling and conditioning properties, as compared to the more efficacious formulation previously disclosed herein. In addition, formulations 52 and 53 had a very poor foaming profile. Similar results were obtained for other anionic surfactants, such as linear alkylbenzene sulfonates, alpha olefin sulfonates, alcohol sulfates, alcohol ether sulfates, etc.

| | Formulation | |
| --- | --- | --- |
| | 52 wt. % (as is) | 53 wt. % (as is) |
| 1. D.I. Water | Q.S. to 100.0 | Q.S. to 100.0 |
| 2. Keltrol RD | 0.8 | 0.8 |
| 3. AEC | 5.3 | — |
| 4. AMPHOSOL ® CA (30%) | 25.0 | 25.0 |
| 5. Ninol 55LL | 2.5 | 2.5 |
| 6. Gantrez AN179 (5%) | 12.0 | 12.0 |
| 7. NaOH (50%) | Q.S. | Q.S. |
| 8. AMMONYX ® CETAC (30%) | 5.8 | 5.8 |
| 9. Mackadet 40K | — | 12.5 |
| 8. Glydant | 0.25 | 0.25 |
| Conditioning Effect on hair | Very Poor | Very Poor |
| Styling/Setting/Body/Stiffness on hair | Very Poor | Very Poor |
| pH | 5.8 | 7.5 |
| Appearance | Translucent | Translucent |
| Foaming | Very Poor | Very Poor |

Without being bound by any particular theory, it is believed that any available anionic surfactant preferentially reacts with the cationic surfactant in the composition to form an undesirable anionic surfactant-cationic surfactant complex, rather than allowing for the formation the desired anionic polymer-cationic styling/conditioning complex in the presence of a non-anionic surfactant system.

Example 6

1. Human Hair Evaluations

Human hair is required for the testing of many personal care compositions and applications, including the compositions of the present invention. The hair also needs to be in a suitable pseudo-realistic form for testing in a laboratory environment. Generally, a swatch of hair glued on to a Plexiglas board for testing. The hair which is typically utilized for testing is 8" European Dark Brown from Demeo Bros. The following test protocol is typically used for the preparation of hair swatches by one skilled in the art.

1. Separate 8" hair into swatches 2.5 grams in weight (for a final weight of 2 grams on a hair swatch that is cut to 6.5" final length).
2. For a different size tress separate 8" hair into swatches 3.5 grams in weight (for a final weight of 3.5 grams on a hair swatch that is cut to 6.5" final length).
3. Wearing gloves, the root end of the hair is glued onto a Plexiglas square. Note: The hair needs to be thoroughly saturated with glue. Glue is applied to the Plexiglas before the hair is laid onto it, and then more glue is applied over the top of the hair as well. On the finished tress board there is usually ⅛" of space left on each side of the Plexiglas board from the hair. The hair is distributed evenly across the board and laid on Saran wrap to dry (this is done to prevent it from inadvertently gluing to the surface it is drying on).

4. The glue is allowed to dry for a minimum of 24 hours.
5. After this period of time, the tress is combed out to untangle and remove any excess hair from the tress board.
6. The hair tress is cut to the appropriate length, usually 6.5" in length from the bottom of the Plexiglas board to the end of the hair. Note: The length of all the tresses is the same. As described in number 1 above where 2.5 grams of 8" hair is cut to 6.5" in length, the final weight of the hair swatch is 2 grams.
7. The hair is washed in a 10% shampoo solution prior to testing or evaluation.

2. Sensory Evaluations

Sensory evaluation are performed in order to determine perceptual performance and property differences between the 3-in-1 hair care compositions of the present invention and leading commercial 2-in-1 conditioning shampoo compositions. A summary of these results is shown in the tables below. The sensory evaluation test methods utilized are as follows:

1. Hair swatches are prepared by weighing 2 g of 8" De Meo Brothers European Natural (virgin) or bleached/waved hair (damaged). The hair is glued on a 1.5"×1.5" plastic tab using Duco cement and allowed to dry for 24 hours.
2. The swatches are cleaned by washing two times with a non-conditioning shampoo and are then allowed to air dry.
3. The hair swatches are then labeled and treated with the appropriate test product (Formulation 46, 47 and a leading commercial 2-in-1 conditioning shampoo):

Approximately 1 g of test hair care composition is applied to wet hair, worked up into a lather using the fingers and allowed to remain on the hair for 60 seconds; the hair swatches are rinsed for 30 seconds under warm running tap water and the treatment repeated a second time.

4. The hair swatches are clipped to a stand and a series of panelists are asked to rate the treated hair swatches for detangling (initial break) and ease of wet combability (course side of a mechanical comb). The rating scale used for these subjective tests was 1=worse (most difficult) and 5=best (easiest). The hair swatches were dried and re-wetted prior to each panelist's evaluation.
5. Treated, dry hair swatches were also rated by a series of panelists for body/style/stiffness, dry combability and static control. The rating scale used for these subjective tests was 1=worse (most difficult) and 5=best (easiest).

As shown in Table #1 and Table #2, Formulations 46 and 47 out-performed the leading commercial non-conditioning base shampoo and the leading commercial styling shampoo, with respect to detangling, wet combability, dry combability, static control and body/style/softness. The leading commercial 2-in-1 conditioning shampoo performed better that the leading commercial non-conditioning base shampoo and the leading commercial styling shampoo, with respect to detangling, wet combability and dry combability. However, the three test compositions were comparable with respect to static control and body/style/softness.

Formulation 46 and 47 out-performed the leading commercial 2-in-1 conditioning shampoo, with respect to detangling, wet combability, dry combability, static control and body/style/softness. The leading commercial base non-conditioning shampoo gave poor performance in all areas overall and was comparable in performance to the leading commercial styling shampoo, with respect to detangling, wet combability, dry combability, static control and body/style/softness.

3. Curl Retention Studies

The curl retention properties of the compositions of the present invention were evaluated and compared to that of leading commercial hair care compositions. It is known to one skilled in the art that curl retention correlates directly with style retention, both of which properties are important from a consumer point-of-view. Curl retention studies allow for the evaluation of concentration effects, temperature effects and/or humidity effects on curl retention properties of various test products.

The procedure used for the curl retention tests performed is as follows. Three hair swatches were prepared for each test product using the same lot of De Meo Brothers natural or damaged hair (bleached/waved) according to the aforementioned procedure for gluing human hair. The swatches are washed two times using a non-conditioning shampoo and allowed to air dry. The hair is wet with luke warm running tap water. Approximately 1 gram of test product is applied to the hair and massaged with the fingers while spreading evenly to cover all of the hair. The test product is left on the hair for 1 minute. The hair is then rinsed for 30 seconds under running tap water. A second 1 gram of test product is applied to the hair and massaged with the fingers while spreading evenly to cover all of the hair. The test product is left on the hair for 1 minute. The hair is then rinsed for 30 seconds under running tap water.

TABLE #1

SENSORY EVALUATION ON HAIR TRESSES BY AN EXPERT PANEL - VIRGIN HAIR

| Attributes | Base Shampoo | | Formulations 46 & 47 | | State of the art shampoos Conditioning | Styling |
|---|---|---|---|---|---|---|
| Detangling | 2.3 | S | 5.0 | S | 3.3 | 2.3 |
| Wet combing | 2.4 | S | 5.0 | S | 3.3 | 2.4 |
| Dry combing | 2.9 | S | 4.0 | S | 3.5 | 2.7 |
| Static control | 2.8 | S | 4.6 | S | 2.8 | 2.6 |
| Body/Style/Stiffness | 1.5 | S | 5.0 | S | 1.4 | 1.5 |

Rating Scale
1 = worst
5 = best
S = significant difference at 95% confidence limit n = 10

TABLE #2

SENSORY EVALUATION ON HAIR TRESSES BY AN EXPERT PANEL - DAMAGED HAIR

| Attributes | Base Shampoo | | Formulations 46 & 47 | | State of the art shampoos Conditioning | Styling |
|---|---|---|---|---|---|---|
| Detangling | 2.0 | S | 5.0 | S | 3.0 | 1.8 |
| Wet combing | 2.2 | S | 5.0 | S | 3.1 | 2.0 |

TABLE #2-continued

SENSORY EVALUATION ON
HAIR TRESSES BY AN EXPERT PANEL - DAMAGED HAIR

| Attributes | Base Shampoo | | Formulations 46 & 47 | | State of the art shampoos | |
|---|---|---|---|---|---|---|
| | | | | | Conditioning | Styling |
| Dry combing | 2.8 | S | 3.9 | S | 3.2 | 2.6 |
| Static control | 2.6 | S | 4.7 | S | 2.7 | 2.4 |
| Body/Style/Stiffiiess | 1.4 | S | 5.0 | S | 1.8 | 1.6 |

Rating Scale
1 = worst
5 = best
S = significant difference at 95% confidence limit n = 10

The hair swatches are curled on a ⅝" roller and are then clipped on a stand which has a vertical numerical scale under each swatch. The swatches allowed to 24 hours at ambient temperature. After this period of time, the rollers are removed, the hair swathes are re-attached to the stand and are placed it into a chamber with a temperature of about 80° F. and relative humidity (RH) of about 90%.

Numerical readings are taken from the vertical scale as to the position of the bottom of the hair (i.e. how much the hair as dropped) initially and after 30, 60, 90, 120, 160, 180, 200 and 240 minute intervals. The percent curl retention for each test swatch is calculated using the following equation:

$$\left(\frac{L - L_t}{L - L_o}\right) \times 100$$

where L=length of hair fully extended $L_o$=initial curl length $L_t$=curl length at a given time t where $L-L_o$ represents the initial amount of curl. The term $L-L_t$ represents the amount of curl at time interval t.

The average percent curl retention is calculated according to the following equation:

Average % curl retention for a test product=$X=x_1+x_2+x_3/3$ where $x_1$, $x_2$ and $x_3$ represents % curl retention for each hair swatch.

The following conclusions can be drawn from the curl retention results depicted in the graphs below, which involve the testing of natural hair (virgin; Table #3) and bleached/waved hair (damaged; Table #4).

TABLE 3

Average % Curl Retention-Damaged Hair
T = 80F % RH = 90.0

| Time (min.) | Leading Protein Shampoo | Leading Curling Shampoo | Leading 2-in-1 Shampoo | Formulations 46 and 47 |
|---|---|---|---|---|
| 0 | 100 | 100 | 100 | 100 |
| 30 | 25 | 30 | 32 | 100 |
| 60 | 20 | 20 | 22 | 98 |
| 90 | 16 | 16 | 18 | 95 |
| 120 | 16 | 16 | 18 | 94 |
| 160 | 16 | 16 | 16 | 92 |
| 180 | 16 | 14 | 14 | 92 |
| 200 | 16 | 14 | 14 | 90 |
| 240 | 12 | 12 | 14 | 90 |

TABLE 4

Average % Curl Retention-Natural Brown Hair
T = 80F % RH = 90.0

| Time (min.) | Leading Protein Shampoo | Leading Curling Shampoo | Leading 2-in-1 Shampoo | Formulations 46 and 47 |
|---|---|---|---|---|
| 0 | 100 | 100 | 100 | 100 |
| 30 | 30 | 35 | 24 | 100 |
| 60 | 20 | 21 | 22 | 99 |
| 90 | 18 | 17 | 22 | 97 |
| 120 | 18 | 17 | 22 | 97 |
| 160 | 18 | 17 | 22 | 96 |
| 180 | 18 | 17 | 20 | 96 |
| 200 | 16 | 17 | 20 | 96 |
| 240 | 14 | 14 | 20 | 96 |

Formulations 46 and 47 of the present invention had far superior average % curl retention at the same time intervals, as compared to the leading commercial 2-in-1 compositions (such as Suave Balsam & Protein Regular Shampoo, Wash-N-Curl, and Pert Plus Shampoo for Normal Hair). The leading commercial 2-in-1 compositions had very poor average % curl retention on both natural and damaged hair. Formulation 46 and 47 performed comparable to a leading commercial non-aerosol hair spray product.

Example 7

Scanning Electron Microscopy Evaluations

Scanning electron microscopy (SEM) was utilized to determine if the three-in-one compositions of the present invention deposition on the hair in the form of a continuous film. Sem allows for comparison of two or more hair samples in terms of deposition of active conditioning/styling agents on the hair. The following procedure was utilized to evaluate test hair samples.

1. The hair sample is mounted on aluminum stubs with sticky tape on both sides.
2. The hair sample is spattered with gold/palladium 60:40 mixture.
3. The sample is placed in a compartment and viewed with a Jeol JM-35C microscope at 5000 magnification.
4. An election beam is introduced which interacts with the topography of the hair fiber. The interaction takes place between the electrons and the gold/palladium metal mixture on the surface of the hair, which serves as an indicator to create the surface image.
5. The resulting surface images are recorded in the form of a photograph.

FIG. I depicts hair treated two times with Formulation # 46; FIG. II depicts hair treated with a leading 2-in-1 conditioning shampoo (Pert Plus Shampoo for Normal Hair).

The areas with high levels of interaction are smooth and appear white in color. This smoothness is an indication that a desirable film deposited on the hair as a result of treatment with the hair care composition. The areas of less interaction or no interaction at all, are dark/black which indicates no deposition of the hair care composition occurred on the hair surface.

The following conclusions can be drawn from the SEM studies and the resulting photographs. Only the hair treated with Formulation 46 which contains both AMMONYX CETAC and Gantrez AN 179 shows significant deposition of styling/conditioning material. Formulation 49 with AMMONYX CETAC and no Gantrez AN179 styling polymer showed deposition on the hair. Formulation 51 with Gantrez AN179 styling polymer and no AMMONYX CETAC quat showed little if any deposition on the hair. Formulation 50 without AMMONYX CETAC quat and Gantrez AN179 styling polymer showed no deposition on the hair. Hair treated two times with a leading commercial 2-in-1 hair care composition (i.e. Pert Plus Shampoo for Normal Hair which contains dimethicone active conditioning agent or Suave Balsam & Protein Regular Conditioner which contains distearyldimonium chloride and cetrimonium chloride quats) showed deposition on the hair.

Example 8

Clear Formulations

| Ingredient | Formulation No. 56 Wt. % as is | Formulation No. 57 Wt. % as is |
|---|---|---|
| D.I. Water | Q.S. to 100.0 | Q.S. to 100.0 |
| Keltrol RD (Xanthan Gum) | — | 0.20 |
| BIO-SOFT ® FF600 ($C_{8-10}$ (5 moles EO) fatty alcohol ethoxylate) | 5.00 | 5.00 |
| Ammonyx ® CDO (30% aqueous) (Cocamidopropylamine Oxide) | 25.00 | — |
| Amphosol ® CA (30% aqueous) (Cocamidopropyl Betaine) | — | 25.00 |
| ACV-4043 (13.12% aqueous) | 4.60 | 4.60 |
| Ninol ® LMP | 2.5 | 2.5 |
| Sodium Hydroxide 50% aqueous | 0.10 | 0.10 |
| Ammonyx ® Cetac 30% aqueous | 5.80 | 5.80 |
| Glydant | 0.25 | 0.25 |
| pH | 5.5–6.5 | 5.5–6.5 |
| Phase type | isotropic liquid | isotropic liquid |

The above formulations are prepared according to the following procedure.

Into a suitable vessel equipped with mixing capability, add D.I. Water. Under agitation, sprinkle in Keltrol RD and mix until a homogeneous dispersion is obtained. Next, add BIOSOFT® FF600 and AMMONYX® CDO, or AMPHOSOL® CA followed by ACV-4043. The pH is adjusted to 6.0–6.3 with sodium hydroxide. The resulting mixture is then heated to 145° F. at which time NINOL® LMP is added, followed by the AMMONYX® CETAC. Mixing is continued 5–10 minutes. Finally, glydant is added and the pH adjusted to between 5.5–6.5.

Example 9

Pearlescent/Opaque Formulations

| Ingredient | Formulation No. 58 Wt. % as is | Formulation No. 59 Wt. % as is |
|---|---|---|
| D.I. Water | Q.S. to 100.0 | Q.S. to 100.0 |
| Keltrol RD (Xanthan Gum) | 0.40 | 0.50 |
| BIO-SOFT ® FF600 ($C_{8-10}$ (5 moles EO) fatty alcohol ethoxylate) | 6.00 | 5.00 |
| AMMONYX ® CDO (30% aqueous) (Cocamidopropylamine Oxide) | 30.00 | — |
| AMPHOSOL ® CA (30% aqueous) | — | 25.00 |

-continued

Pearlescent/Opaque Formulations

| Ingredient | Formulation No. 58 Wt. % as is | Formulation No. 59 Wt. % as is |
|---|---|---|
| (Cocamidopropyl Betaine) | | |
| ACV-4043 (13.12% aqueous) | 4.40 | 4.40 |
| Sodium Hydroxide 50% aqueous | 0.10 | 0.10 |
| Ninol ® LMP (Lauric/Myristic MEA) | 3.00 | 2.50 |
| AMMONYX ® Cetac 30% aqueous (Cetrimonium Chloride) | 5.80 | 5.80 |
| KESSCO ® EGDS (Glycol Distreate) | 1.25 | 1.25 |
| Glydant | 0.25 | 0.25 |
| pH | 6.3–6.8 | 6.3–6.8 |
| Phase type | isotropic liquid | isotropic liquid |
| Appearance | pearlescent/opaque | pearlescent/opaque |

The above formulations are prepared according to the following procedure. To a suitable vessel equipped with mixing, heating, and cooling capabilities is added D.I. water and, with agitation set at high speed, Keltrol RD slowly added. The compositon is mixed until a homogeneous dispersion is obtained. Next the dispersion is heated to about 73° C. (165° F.) and BIO-SOFT FF600 and AMMONYX CDO or AMPHOSOL CA added, followed by ACV-4043. The pH is next adjusted to 6.3–6.8 with sodium hydroxide 50%, after which AMMONYX CETAC, NINOL LMP, and KESSCO EGDS are added and the composition mix for an additional 20–30 minutes. Finally, the mixture is cooled to ambient temperature, Glydant added, and the pH adjusted to 6.3–6.8.

Example 10

Non-Aerosol Hairspray

Non-Aerosol Hairspray

| | Formulation No. | | |
|---|---|---|---|
| | 60 weight % | 61 weight % | 62 weight % |
| Ethanol | 88.7 | 10.4 | 66.82 |
| ACV-4043 copolymer (13.63% aqueous) | 4.5 | 37.4 | 18.71 |
| 1-Amino-2-methylpropan-3-ol | | 4.0 | 2.00 |
| AMMONYX CETAC (30% aqueous) | 5.8 | 48.2 | 12.5 |
| pH | 6.6 | 8.2 | 6.6 |
| Appearance | Clear | Hazy | Clear |

Example 11

Pearlescent/Opaque Formulations

| Ingredient | Formulation No. 63 Wt. % as is | 64 Wt. % as is |
|---|---|---|
| D.I. Water | Q.S. to 100.0 | Q.A. to 100.0 |
| Keltrol RD (Xanthan Gum) | 0.40 | 0.50 |
| BIO-SOFT ® FF600 ($C_{8-10}$ (5 moles EO) fatty alcohol ethoxylate) | 6.00 | 5.00 |
| AMMONYX ® CDO (30% aqueous) (Cocamidopropylamine Oxide) | 30.00 | — |
| AMPHOSOL ® CA (30% aqueous) (Cocamidopropyl Betaine) | — | 25.00 |
| ACV-4043 (13.12% aqueous) | 1.1 | 1.1 |
| Sodium Hydroxide 50% aqueous | 0.02 | 0.02 |
| Ninol ® LMP (Lauric/Myristic MEA) | 3.00 | 2.50 |
| AMMONYX ® Cetac 30% aqueous (Cetrimonium Chloride) | 1.45 | 1.45 |
| KESSCO ® EGDS (Glycol Distreate) | 1.25 | 1.25 |
| Glydant | 0.25 | 0.25 |
| pH | 6.3–6.8 | 6.3–6.8 |
| Phase type | isotropic liquid | isotropic liquid |
| Appearance | pearlescent/ opaque | pearlescent/ opaque |

From the foregoing, it will be appreciated that although specific embodiments of the invention have been described herein for purposes of illustration, various modifications may be made without deviating from the spirit or scope of the invention.

What is claimed is:

1. A method for cleaning, conditioning and styling hair comprising:
   (i) applying to wet hair a composition comprising:
      (a) from about 8 percent to about 25 percent by weight, based on the total weight of the hair care composition, of a surfactant mixture comprising at least one nonionic surfactant and at least one amphoteric surfactant;
      (b) from about 1 percent to about 3 percent by weight, based on the total weight of the hair care composition, of a cationic surfactant selected from the group consisting of di- (hydrogenated tallow) dimethyl ammonium chloride, dioctadecyl dimethyl ammonium chloride, stearyl dimethyl benzyl ammonium chloride, dicetyl dimethyl ammonium chloride, cetyl trimethyl ammonium chloride, tricetyl methyl ammonium chloride, methyl bis- (hydrogenated tallowamidoethyl) 2-hydroxyethyl ammonium methyl sulfate, and mixtures thereof;
      (c) from about 0.3 percent to about 2 percent by weight, based on the total weight of the hair care composition, of an anionic polymer selected from the group consisting of polymeric condensation products of methyl vinyl ether and maleic anhydride, and salts, half acid esters, half acid amides, salts of the half acid esters, and salts of the half amide esters thereof, and mixtures thereof;
      wherein the anionic polymer and the cationic surfactant are capable of combining to form a complex;
   (ii) forming a lather of the composition on the wet hair;
   (iii) rinsing the lather from the hair; and
   (iv) arranging the hair into a desired configuration whereby the hair will maintain the desired configuration.

2. A method according to claim 1, where the hair care composition further comprises from about 0–1 percent to about 10 percent by weight, based on the total weight of the hair care composition, of a swellable polymer thickening agent.

3. A method according to claim 2, where the hair care composition comprises from about 0.2 percent to about 3.0 percent by weight based on the total weight of the hair care composition of the swellable polymer thickening agent.

4. A method according to claim 3, where the hair care composition comprises from about 0.2 percent to about 2.0 percent by weight, based on the total weight of the hair care composition of the swellable polymer thickening agent.

5. A method according to claim 2, wherein the swellable polymer thickening agent is selected from the group consisting of methyl cellulose, ethyl cellulose, xanthan gum, gum arabic, gum karaya, guar gum, locust bean gum, ghatti gum, hydrolyzed starches, low molecular weight ethylene oxide polymers, low molecular weight propylene oxide polymers and mixtures thereof.

6. A method according to claim 1, wherein the hair care composition comprises from about 10 percent to about 25 percent by weight, based on the total weight of the hair care composition, of the surfactant mixture.

7. A method according to claim 1, wherein the nonionic surfactant is selected from the group consisting of polyoxyethyleneated straight chain alcohols, primary alkanolamides, ethoxylated primary alkanolamides, alkylpolyglycosides, alkylpolysaccharides, polyhydroxy fatty acid amides, and amine oxides and mixtures thereof.

8. A method according to claim 7, wherein the nonionic surfactant is selected from the group consisting of polyoxyethyleneated straight chain alcohols, primary alkanolamides, alkylpolysaccharides, and amine oxides and mixtures thereof.

9. A method according to claim 1, wherein the amphoteric surfactant is selected from the group consisting of betaines, sulfobetaines, amidopropyl betaines, cocobetaines, cocoamidopropyl betaines, lauryl betaines, lauramidopropyl betaines, and sultaines and mixtures thereof.

10. A method according to claim 9, wherein the amphoteric surfactant is selected from the group consisting of cocoamidopropyl betaines, and sulfobetaines and mixtures thereof.

11. The method according to claim 1, wherein the surfactant mixture further comprises a semi-polar nonionic surfactant selected from the group consisting of long-chain amine oxides having the formula

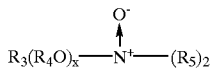

wherein $R_3$ is an alkyl, hydroxyalkyl, acylamidopropyl or alkyl phenyl group;

each $R_4$ is independently an alkylene or hydroxyalkylene group;

x is from about 0–3; and each $R_5$ is independently an alkyl or hydroxyalkyl group; and wherein the $R_5$ groups can be attached to each other, either by an oxygen or nitrogen atom to form a ring structure and mixtures thereof.

12. A method according to claim 11, wherein the amine oxide is selected from the group consisting of $C_{10}$–$C_{18}$ alkyl dimethyl amine oxides, a $C_8$–$C_{12}$ alkoxy ethyl dihydroxyethyl amine oxides, and dimethyldodecylamine oxides and mixtures thereof.

13. A method according to claim 1, wherein the cationic surfactant is selected from the group consisting of stearyl dimethyl benzyl ammonium chloride, cetyl trimethyl ammonium chloride, dicetyl dimethyl ammonium chloride and mixtures thereof.

* * * * *